United States Patent
Wayne et al.

(10) Patent No.: US 10,729,512 B2
(45) Date of Patent: Aug. 4, 2020

(54) METHODS AND APPARATUS FOR COUPLING AN OPTICAL INPUT TO AN ILLUMINATION DEVICE

(71) Applicant: Invuity, Inc., San Francisco, CA (US)

(72) Inventors: David Wayne, Watsonville, CA (US); Alex Vayser, Mission Veijo, CA (US); Douglas Rimer, Los Altos Hills, CA (US); Fernando Erismann, New York, NY (US); Gaston Tudury, San Francisco, CA (US); Michael Boutillette, San Francisco, CA (US); Aaron Weiss, Oakland, CA (US); Vladimir Zagatsky, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

(21) Appl. No.: 16/601,164

(22) Filed: Oct. 14, 2019

(65) Prior Publication Data

US 2020/0038135 A1 Feb. 6, 2020

Related U.S. Application Data

(60) Continuation of application No. 16/376,681, filed on Apr. 5, 2019, now Pat. No. 10,512,520, which is a
(Continued)

(51) Int. Cl.
*A61B 90/30* (2016.01)
*A61B 17/02* (2006.01)
(Continued)

(52) U.S. Cl.
CPC .............. *A61B 90/30* (2016.02); *A61B 5/00* (2013.01); *A61B 17/02* (2013.01); *A61B 2017/00477* (2013.01); *A61B 2090/306* (2016.02)

(58) Field of Classification Search
None
See application file for complete search history.

(56) References Cited

U.S. PATENT DOCUMENTS

| | | | |
|---|---|---|---|
| 6,322,499 | B1 | 11/2001 | Evans et al. |
| 8,088,066 | B2 | 1/2012 | Grey et al. |
| | | (Continued) | |

FOREIGN PATENT DOCUMENTS

| | | | |
|---|---|---|---|
| EP | 1028341 | A2 | 8/2000 |
| EP | 2320967 | A2 | 5/2011 |
| | (Continued) | | |

OTHER PUBLICATIONS

International search report with written opinion dated Mar. 31, 2016 for PCT/US2015/063532.
(Continued)

*Primary Examiner* — Jerry Rahll
(74) *Attorney, Agent, or Firm* — McDonnell Boehnen Hulbert & Berghoff LLP

(57) ABSTRACT

A surgical illumination apparatus comprises a fiber optic input, and illuminated surgical instrument, and an optical coupling bracket for coupling the fiber optic input to the illuminated surgical instrument. The coupling bracket comprises an elongate frame having a proximal end, a distal end, and a central channel extending therebetween, wherein the central channel is sized to receive and support optical fibers of the fiber optic input. The proximal end of the bracket is coupled to the fiber optic input, and the distal end of the bracket is coupled to an illumination element of the illuminated surgical instrument. The apparatus may further comprise a shroud disposed around the illumination element that is coupled to the bracket.

20 Claims, 23 Drawing Sheets

Related U.S. Application Data division of application No. 14/957,452, filed on Dec. 2, 2015, now Pat. No. 10,321,969.

(60) Provisional application No. 62/086,653, filed on Dec. 2, 2014.

(51) Int. Cl.
*A61B 5/00* (2006.01)
*A61B 17/00* (2006.01)

(56) References Cited

U.S. PATENT DOCUMENTS

| | | |
|---|---|---|
| 8,409,088 B2 | 4/2013 | Grey et al. |
| 2006/0133737 A1 | 6/2006 | Gallup et al. |
| 2011/0319720 A1 | 12/2011 | Grey et al. |
| 2013/0324801 A1 | 12/2013 | Grey et al. |
| 2014/0029290 A1 | 1/2014 | Kazakevich |
| 2014/0049979 A1 | 2/2014 | Vayser et al. |
| 2014/0221763 A1 | 8/2014 | Vayser et al. |

FOREIGN PATENT DOCUMENTS

| | | |
|---|---|---|
| EP | 2638876 A2 | 9/2013 |
| GB | 2133694 A | 8/1984 |

OTHER PUBLICATIONS

European search report with written opinion dated Jan. 10, 2018 for EP Application No. 15865818.

VIEW B-B

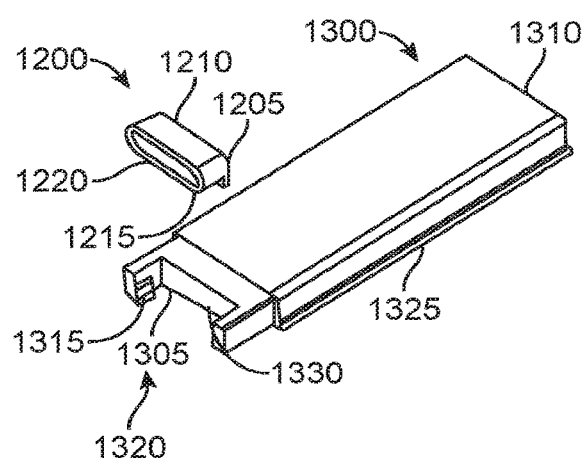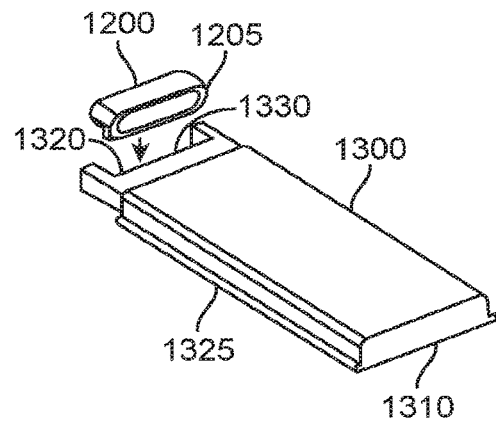
FIG. 12A  FIG. 12B
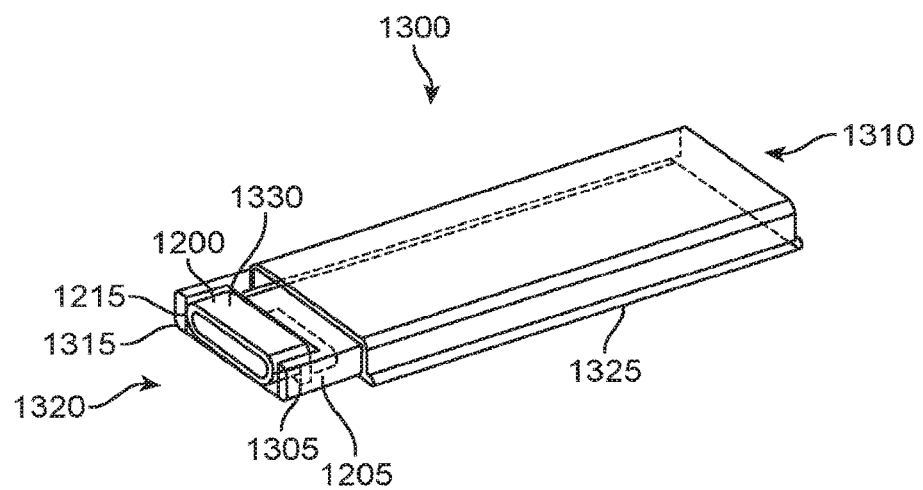
FIG. 12C

METHODS AND APPARATUS FOR COUPLING AN OPTICAL INPUT TO AN ILLUMINATION DEVICE

CROSS-REFERENCE TO RELATED APPLICATIONS

The present application is continuation of U.S. patent application Ser. No. 16/376,681, filed Apr. 5, 2019, which is a divisional of U.S. patent application Ser. No. 14/957,452, filed Dec. 2, 2015 (issued as U.S. Pat. No. 10,321,969 on Jun. 18, 2019), which claims the benefit of US Provisional Patent Application No. 62/086,653 filed on Dec. 2, 2014; the entire contents of which are incorporated herein by reference.

This application is related to the following co-pending U.S. patent application Ser. Nos. 11/923,483; 14/035,583; 14/264,406; the entire contents of which are incorporated herein by reference.

BACKGROUND OF THE INVENTION

The devices, systems and methods described below relate generally to illuminated devices such as medical devices, systems, and methods and preferably relate to illumination of a surgical field, although this is not intended to be limiting and usage outside of a surgical field is also contemplated.

Illumination of target areas to allow an operator to clearly observe the target area can be challenging. External lighting provided by headlamps or wall mounted lights require constant adjustment and can still cast unwanted shadows in the target area. These devices may be heavy and can be uncomfortable to wear. Additionally, these illumination techniques may not be capable of illuminating a target area that is deep and disposed far below a surface such as a surgical field in a patient. Other illumination techniques may use an illumination element such as a fiber optic bundle which can be coupled to tools or other instruments and which are inserted into the target area thereby providing more localized illumination. Examples of this approach include surgical retractor blades with fiber optics or other illumination elements coupled thereto. Fiber optics can help illuminate the target area, but fiber optic systems can also be inefficient at transmitting light, and the resulting light loss significantly reduces the amount of light delivered to the target area. Powerful light sources may be provided in an attempt to overcome the inefficiency of light transmission, but such attempts can result in excessive heat generation, potentially leading to fires or thermal damage to the patient or surgical instruments being used.

In addition to the challenges associated with the techniques described above, illuminated tools and instruments must not only provide adequate illumination of the work area, but they preferably must also be able to access tight spaces without occupying significant volume that otherwise is needed for other tools and instruments, or an operator's hands, as well as still allowing the operator an unobstructed view of the working area. With the introduction of newer minimally invasive surgical techniques, it has become especially important to provide illumination systems with low profiles, so that the systems may be used in conjunction with minimal surgical incisions.

In order to keep the profile of an illumination system as minimal as possible, the optical coupling between the illumination input (e.g. a fiber optic input cable or other input) and the illumination element (e.g. a fiber optic or an optical waveguide) is preferably in a low-profile configuration. Furthermore, it would be desirable for such a low-profile optical coupling to have robust structural support, both to secure the attachment of the optical input to the illumination element, as well as protecting the coupling between the optical input and illumination element from excessive flexural loads and stresses that could disrupt the light input. It would also be desirable to provide an optimized coupling between the optical input and the illumination element that is optically efficient to minimize light loss and resulting localized heating. In manufacturing such a low-profile illumination system, it would also be desirable to provide a structure and method for facilitating the handling of the optical input (e.g. fiber optic input cable) during manufacturing and assembly processes. At least some of these objectives will be met by the exemplary embodiments described herein.

SUMMARY OF THE INVENTION

Aspects of the present disclosure provide an apparatus and method for coupling an optical input to an illumination element that is preferably coupled to a surgical instrument in a low-profile configuration.

In a first aspect of the present disclosure, a surgical illumination apparatus for illuminating a surgical field in a patient comprises a fiber optic input, an illuminated surgical instrument, and an optical coupling bracket for coupling the fiber optic input to the illuminated surgical instrument. The illuminated surgical instrument comprises a surgical device and an illumination element coupled thereto, wherein the illumination element is coupled with the fiber optic input and configured to emit light from the fiber optic input toward the surgical field. The optical coupling bracket comprises an elongate frame having a proximal end, a distal end, and a central channel extending therebetween. The central channel is defined by an upper surface, a lower surface, and two side walls, and is sized to receive and support the optical fibers of the fiber optic input. The distal end of the optical coupling bracket is coupled to the illumination element.

The bracket may comprise one or more protruding members configured to engage the fiber optic input. The protruding members may be disposed on the proximal end of the frame, adjacent both side walls of the central channel, extending in a direction transverse to the longitudinal axis of the frame.

The bracket may further comprise one or more engagement elements configured to engage the illumination element. The engagement elements may be disposed on the distal end of the frame, and may comprise one or more holes configured to capture pins, screws, or protrusions disposed on the proximal end of the illumination element.

One of the bracket or the illumination element may further comprise a protrusion, and the other of the bracket or the illumination element may comprise a receptacle. The protrusion may be configured to snap fit into the receptacle to couple the bracket to the illumination element.

The one or more optical fibers of the fiber optic input may be captured by the central channel of the bracket to couple the fiber optic input to the bracket. The optical fibers may be arranged in one or more linear arrays that are vertically stacked atop one another, so as to have a low-profile configuration. An adhesive may be disposed in the central channel to fixedly couple the optical fibers to the frame.

The illumination element may comprise an optical waveguide, configured to transmit light from the fiber optic input to the surgical field, directing the light to the surgical field through light-emitting surfaces having surface features configured to extract and direct the light. The optical waveguide may comprise a pocket disposed on the proximal end, where the pocket may be configured to receive the fiber optic input. The optical waveguide may further comprise a pocket disposed on the proximal end, where the pocket may be configured to receive at least the distal end of the coupling bracket.

One of the optical waveguide or the surgical instrument may further comprise a protrusion and the other of the waveguide or the surgical instrument may comprise a matching receptacle. The protrusion may be configured to slide into the receptacle to couple the waveguide to the instrument. The protrusion may have a dovetail shape and the matching receptacle may be a dovetail-shaped groove.

The surgical illumination apparatus may further comprise a shroud coupled to an optical waveguide, wherein the shroud is disposed around at least a portion of the perimeter of the optical waveguide. The shroud may have one or more openings on a top surface, a bottom surface, or on both the top and the bottom surfaces, through which the light-emitting surfaces of the optical waveguide can transmit light to the surgical field. The shroud may be configured to maintain an air gap between the shroud and the waveguide, so as to minimize interference with light propagation within the waveguide (e.g. due to light loss). The shroud may further comprise one or more magnets integrated with the shroud, wherein the magnets may be configured to magnetically couple the shroud with the surgical device.

The surgical illumination apparatus may further comprise a collar disposed over the coupling bracket, at least a portion of the fiber optic input, and at least a portion of the illumination element. One of the collar or the coupling bracket may comprise a protrusion, and the other of the collar or the coupling bracket may comprise a receptacle. The protrusion may be configured to snap fit into the receptacle to couple the collar to the coupling bracket. One of the collar or the illumination element may comprise a protrusion, and the other of the collar or the illumination element may comprise a receptacle. The protrusion may be configured to snap fit into the receptacle to couple the collar to the illumination element.

The collar may be configured to slide axially over the coupling bracket, at least a portion of the fiber optic input, and at least a portion of the illumination element. The collar may be adhesively coupled or otherwise adhered to at least one of the coupling bracket, the fiber optic input, or the illumination element. Methods for adhesion may comprise press-fitting, crimping, welding, and other methods known in the field.

The surgical illumination apparatus may further comprise an articulated track attachment for attaching the fiber optic input to the surgical instrument. The articulated track attachment may comprise a proximal end, a distal end, a bottom surface, a top surface, and two sides, and may further comprise a plurality of rails separated by alternating slots and aligned to form a flexible track that extends between the proximal and distal ends. The articulated track may be configured to conform to angles of between −180 and 180 degrees, wherein an angle of 0 degrees corresponds to an unflexed flat position. The proximal and distal ends of the articulated track attachment may each comprise a coupling element configured to receive the fiber optic input and to attach to the surgical instrument. The articulated track attachment may comprise a plurality of protrusions aligned on each side to form a central channel and configured to receive the fiber optic input.

One of the articulated track attachment or the surgical instrument may comprise a protrusion, and the other of the articulated track attachment or the surgical instrument may comprise a receptacle. The protrusion may be configured to snap fit into the receptacle to attach the articulated track attachment to the surgical instrument. The surgical instrument may comprise a camera, a sensor or a retractor.

In another aspect of the present invention, an optical coupling bracket for optically coupling an illuminated surgical instrument with a fiber optic input comprises an elongate frame having a proximal end, a distal end, and a central channel extending therebetween. The central channel is defined by an upper surface, a lower surface, and two side walls, and the channel is sized to receive and support the optical fibers of the fiber optic input. The central channel may be configured to capture optical fibers arranged in one or more linear arrays that are vertically stacked atop one another. The bracket may comprise one or two protruding members (also referred to as legs) configured to engage the fiber optic input, the protruding members disposed on the proximal end of the frame and extending in a direction transverse to the longitudinal axis of the frame. The bracket may further comprise one or more engagement elements configured to engage an illumination element of the illuminated surgical instrument, wherein the engagement elements are disposed on the distal end of the frame. The engagement elements may comprise one or more holes configured to capture one or more pins, screws, or protrusions of the illumination element. One of the bracket or the illumination element may comprise a protrusion or a receptacle, and the other of the bracket or the illumination element may comprise a matching receptacle or matching protrusion. The protrusion may be configured to snap fit into the receptacle to couple the bracket to the illumination element.

In another aspect of the present invention, a method for coupling a light input element such as a fiber optic input to an illuminated surgical instrument comprises providing the illuminated surgical instrument and an optical coupling bracket, disposing the fiber optic input in the bracket, coupling the fiber optic input to the illuminated surgical instrument, and coupling the bracket to the illuminated surgical instrument.

The illuminated surgical instrument may comprise a surgical device and an illumination element coupled thereto, and the bracket may comprise a frame having a proximal end, a distal end, and a central channel extending therebetween, sized to receive and support the one or more optical fibers of the fiber optic input, and disposing the fiber optic input in the bracket may comprise disposing the fiber optic input in the central channel. Coupling the fiber optic input to the illuminated surgical instrument may comprise coupling the fiber optic input to the illumination element.

The fiber optic input may comprise one or more optical fibers, and disposing the fiber optic input in the channel may comprise arranging the one or more optical fibers of the fiber optic input in one or more linear arrays that are vertically stacked atop one another. The linear arrays may be staggered relative to one another such that the outer surface of one fiber may fit in a trough created by two adjacent fibers in an adjacent linear array. The optical fibers or the fiber optic input may be adhesively or otherwise fixedly coupled to the frame of the bracket by disposing an adhesive in the central channel of the optical coupling bracket. The method may further comprise trimming or polishing the one or more optical fibers disposed in the channel.

The bracket may comprise protruding members configured to engage the optical input, and the optical fibers may be aligned substantially parallel to the protruding members and inserted into the channel. A band may be placed around the protruding members and the optical fibers disposed therebetween, so as to couple the optical fibers and the bracket in a stable configuration.

The illumination element may comprise an optical waveguide having a pocket disposed on the proximal end, and coupling the fiber optic input to the illumination element may comprise inserting the distal end of the fiber optic input into the pocket.

The bracket may further comprise one or more engagement elements, and coupling the bracket to the illumination element may comprise adhesively bonding the distal end of the bracket frame to the illumination element, or engaging one or more of the engagement elements of the bracket to the illumination element. The engagement elements may comprise one or more holes disposed on the distal end of the bracket frame, and they may be engaged to the illumination element via one or more pins, screws, or protrusions of the illumination element. Coupling the bracket to the illumination element may further comprise snap fitting the bracket to the illumination element.

The method may further comprise providing a shroud, where the illumination element comprises an optical waveguide and the shroud is disposed around the optical waveguide. The method also comprises coupling the optical coupling bracket to the shroud. The bracket and the shroud may be formed from a metal material, and one or more surfaces of the distal end of the bracket frame may be welded to one or more interior surfaces of the shroud.

The method may further comprise magnetically coupling the shroud to the surgical device. The shroud may comprise one or more magnets that are integrated with or coupled to one or more surfaces of the shroud, wherein the magnets may be coupled to a magnetic surface of the surgical device. Alternatively, the shroud may comprise a magnetic material that can be coupled to one or more magnets integrated with or coupled to one or more surfaces of the surgical device.

The illumination element may comprise an optical waveguide having a pocket disposed on the proximal end, and coupling the bracket to the illumination element may comprise inserting at least the distal end of the coupling bracket into the pocket of the optical waveguide.

One of the coupling bracket or the illumination element may comprise a protrusion, and the other of the coupling bracket or the illumination element may comprise a receptacle. The protrusion may be configured to snap fit into the receptacle to couple the coupling bracket to the illumination element.

The method may further comprise providing a collar, and disposing the collar over the illumination element, the coupling bracket, and the fiber optic input. One of the collar or the coupling bracket may comprise a protrusion, and the other of the collar or the coupling bracket may comprise a receptacle. The method may further comprise snap-fitting the protrusion into the receptacle to couple the collar to the coupling bracket. The method may further comprise sliding the collar over at least a portion of the illumination element and the coupling bracket and adhesively coupling the collar to at least one of the illumination element or the coupling bracket. The collar may be adhesively coupled or otherwise adhered to at least one of the coupling bracket, the fiber optic input, or the illumination element. Methods for adhesion may comprise press-fitting, crimping, welding, and other methods known in the field.

In still another aspect of the present invention, a method for coupling an illumination element to a surgical device, comprises providing an illumination element, providing a surgical device, and coupling the illumination element to the surgical device. One of the illumination element or the surgical device may comprise a protrusion and the other of the illumination element or the surgical device may comprise a matching receptacle. The protrusion may be configured to slide into the receptacle to couple the illumination element to the surgical device. The illumination element may comprise an optical waveguide, and the method may further comprise coupling the optical waveguide to the surgical instrument. The protrusion may have a dovetail shape and the matching receptacle may be a dovetail-shaped groove. The surgical instrument may comprise a camera, a sensor or a retractor. Obtaining a surgical device may comprise obtaining a camera, a sensor or a retractor.

In still another exemplary embodiment of the present disclosure, a surgical illumination device for providing light to a surgical field in a patient comprises an illumination element, an optical coupling bracket, and a light input element. The illumination element has a proximal portion and a distal portion. The distal portion comprises optical structures for extracting light from the illumination element and directing the extracted light toward the surgical field. The proximal portion comprises a first leg and a second leg. The legs extend proximally and are disposed on opposite lateral sides of the proximal portion of the illumination element. The proximal portion further comprises a receptacle that is defined by a space disposed between the first leg, the second leg, and a proximal-most end of the illumination element. The optical coupling bracket has a proximal region, a distal region, and a central channel disposed therebetween. The distal region is at least partially disposed in the receptacle, and the coupling bracket is coupled to the illumination element. A distal portion of the light input element is disposed in the central channel of the coupling bracket, and the light input element is configured to provide light from a light source to the illumination element.

The illumination element may be a non-fiber optic optical waveguide. Light may be transmitted through the optical waveguide by total internal reflection. The optical structures may comprise a plurality of facets or a plurality of stair steps, each stair step having a ramp and a step, and an angle between the ramp and the step. The ramp may be a substantially flat planar surface, and the step may be a substantially flat planar surface. The ramp may be disposed at an angle that promotes total internal reflection of the light in the optical waveguide, and the step may be disposed at an angle that promotes extraction of the light from the optical waveguide. The distal-most end of the illumination element may comprise optical structures configured for extracting the light therefrom and directing the light to the surgical field.

The optical waveguide may further comprise a pocket disposed on the proximal portion and the pocket may be configured to receive at least the distal region of the coupling bracket.

One of optical waveguide or the surgical instrument may further comprise a protrusion and the other of the waveguide or the surgical instrument may comprise a matching receptacle. The protrusion may be configured to slide into the receptacle to couple the waveguide to the instrument. The protrusion may have a dovetail shape and the matching receptacle may be a dovetail-shaped groove.

The coupling bracket may comprise a keyway element, and the optical waveguide may comprise a keyway element having a shape that cooperates with the coupling bracket keyway element to ensure proper alignment of the coupling bracket with the optical waveguide. The light input element may comprise a plurality of optical fibers. The plurality of fibers each may have a distal end, and the distal ends may be substantially flush with one another. The plurality of fibers may form a substantially flat planar ribbon. A sheath may be disposed over the plurality of fibers.

The coupling bracket may further comprise an engagement element disposed adjacent the distal region, and the illumination element may comprise an engagement element configured to engage with the coupling bracket engagement element.

One of the coupling bracket or the illumination element of the device may comprise a protrusion, and the other of the coupling bracket or the illumination element may comprise a receptacle. The protrusion may be configured to snap fit into the receptacle to couple the bracket to the illumination element.

The central channel of the coupling bracket may have a substantially parallelogram shaped cross-section. The coupling bracket may be adhesively coupled to the illumination element. The coupling bracket may be releasably coupled to the illumination element. One of the bracket or the illumination element may further comprise a protrusion, and the other of the bracket or the illumination element may comprise a receptacle. The protrusion may be configured to snap fit into the receptacle to couple the bracket to the illumination element.

The device may further comprise an instrument that is coupled to the illumination element. The instrument may be a surgical instrument such as a surgical retractor, a tool, or any other instrument.

The device may further comprise a collar disposed over the coupling bracket, at least a portion of the fiber optic input, and at least a portion of the illumination element. One of the collar or the coupling bracket may comprise a protrusion, and the other of the collar or the coupling bracket may comprise a receptacle. The protrusion may be configured to snap fit into the receptacle to couple the collar to the coupling bracket. The collar may be configured to slide over at least a portion of the illumination element and the coupling bracket. The collar may be adhesively coupled or otherwise adhered to at least one of the coupling bracket, the light input element, or the illumination element. Methods for adhesion may comprise press-fitting, crimping, welding, and other methods known in the field.

The device may further comprise a surgical instrument and an articulated track attachment for attaching the light input element to the surgical instrument. The articulated track attachment may comprise a proximal end, a distal end, a bottom surface, a top surface, and two sides. A plurality of rails separated by alternating slots and aligned to form a flexible track may extend between the proximal and distal ends. The articulated track may be configured to conform to angles of between −180 and 180 degrees, wherein an angle of 0 degrees corresponds to an unflexed flat position. The proximal and distal ends may each comprise a coupling element configured to receive the light input element and to attach to the surgical instrument.

The articulated track attachment may further comprise a plurality of protrusions aligned on each side of the track to form a central channel and configured to receive the light input element. One of the articulated track attachment or the surgical instrument may comprise a protrusion, and the other of the articulated track attachment or the surgical instrument may comprise a receptacle. The protrusion may be configured to snap fit into the receptacle to couple the articulated track attachment to the surgical instrument.

In another aspect of the present invention, an articulated track attachment device for attaching a fiber input element to a surgical instrument may comprise a proximal end, a distal end, a bottom surface, a top surface, and two sides. A plurality of rails separated by alternating slots and aligned to form a flexible track may extend between the proximal and distal ends of the device. The articulated track may be configured to conform to angles of between −180 and 180 degrees, wherein an angle of 0 degrees corresponds to an unflexed flat position. The proximal and distal ends may each comprise a coupling element configured to receive the fiber input element and to attach to the surgical instrument.

The articulated track attachment device may attach a fiber optic input to a surgical instrument. The articulated track attachment device may further comprise a plurality of protrusions aligned on each side of the device to form a central channel and configured to receive the fiber optic input. One of the articulated track attachment device or the surgical instrument may comprise a protrusion, and the other of the articulated track attachment device or the surgical instrument may comprise a receptacle. The protrusion may be configured to snap fit into the receptacle to couple the articulated track attachment device to the surgical instrument. The surgical instrument may comprise a camera, a sensor or a retractor.

In yet another aspect of the present invention, a method of attaching a fiber input element to a surgical instrument comprises providing a fiber input element and a surgical instrument, providing an articulated track attachment device, disposing the fiber input element in the articulated track attachment device, and attaching the articulated track attachment device to the surgical instrument.

The fiber input element may comprise a fiber optic input and attaching the articulated track attachment device to the surgical instrument may comprise coupling a proximal end of the device to the surgical instrument and coupling a distal end of the device to the surgical instrument. One of the articulated track attachment device or the surgical instrument may comprise a protrusion, and the other of the articulated track attachment device or the surgical instrument may comprise a receptacle. Attaching the articulated track attachment device to the surgical instrument may comprise snap fitting the protrusion into the receptacle. The method may further comprise flexing the articulated track attachment device to an angle of between −180 and 180 degrees, wherein an angle of 0 degrees corresponds to an unflexed flat position. The surgical instrument may comprise a camera, a sensor or a retractor.

These and other embodiments are described in further detail in the following description related to the appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A shows a perspective view of an alternative embodiment of an illumination element and a coupling bracket.

FIG. 12B shows engagement of the bracket and illumination element illustrated in FIG. 12A.

FIG. 12C shows the bracket and illumination element of FIG. 12A coupled together.

DETAILED DESCRIPTION OF THE INVENTION

The method and apparatus as disclosed herein are suited for use with any illumination element coupled with a light input element such as a fiber optic input but will be described specifically for use with surgical devices, including surgical retractors and suction devices. They are especially well-suited for low-profile devices to be used in minimally or less invasive surgeries, where the surgical operations are performed within narrow cavities formed from minimal surgical incisions.

An optical waveguide as described herein may transmit light from an illumination input such as a fiber optic input through the waveguide by total internal reflection. The light can be extracted from the waveguide via one or more surface features disposed on one or more surfaces of the waveguide. The waveguide may also comprise an angled distal tip for directing the remaining light that has not been extracted by the surface features to the surgical field. The light-emitting surfaces of the waveguide can control the direction of the extracted light, such that the light illuminates the surgical field. An exemplary embodiment of the optical waveguide and its features are described in greater detail in U.S. patent application Ser. Nos. 11/654,874, 11/923,483, and 14/035,583, the entire contents of which are incorporated herein by reference. Any of the features described in the above mentioned references incorporated herein by reference may be used in combination with or as a substitution for any of the features described in this specification.

While the illumination element as described herein often comprises an optical waveguide, one of skill in the art will appreciate that any number of illumination elements such as LED lights, incandescent lights, or fiber optics may be used instead of an optical waveguide.

Figure 1:
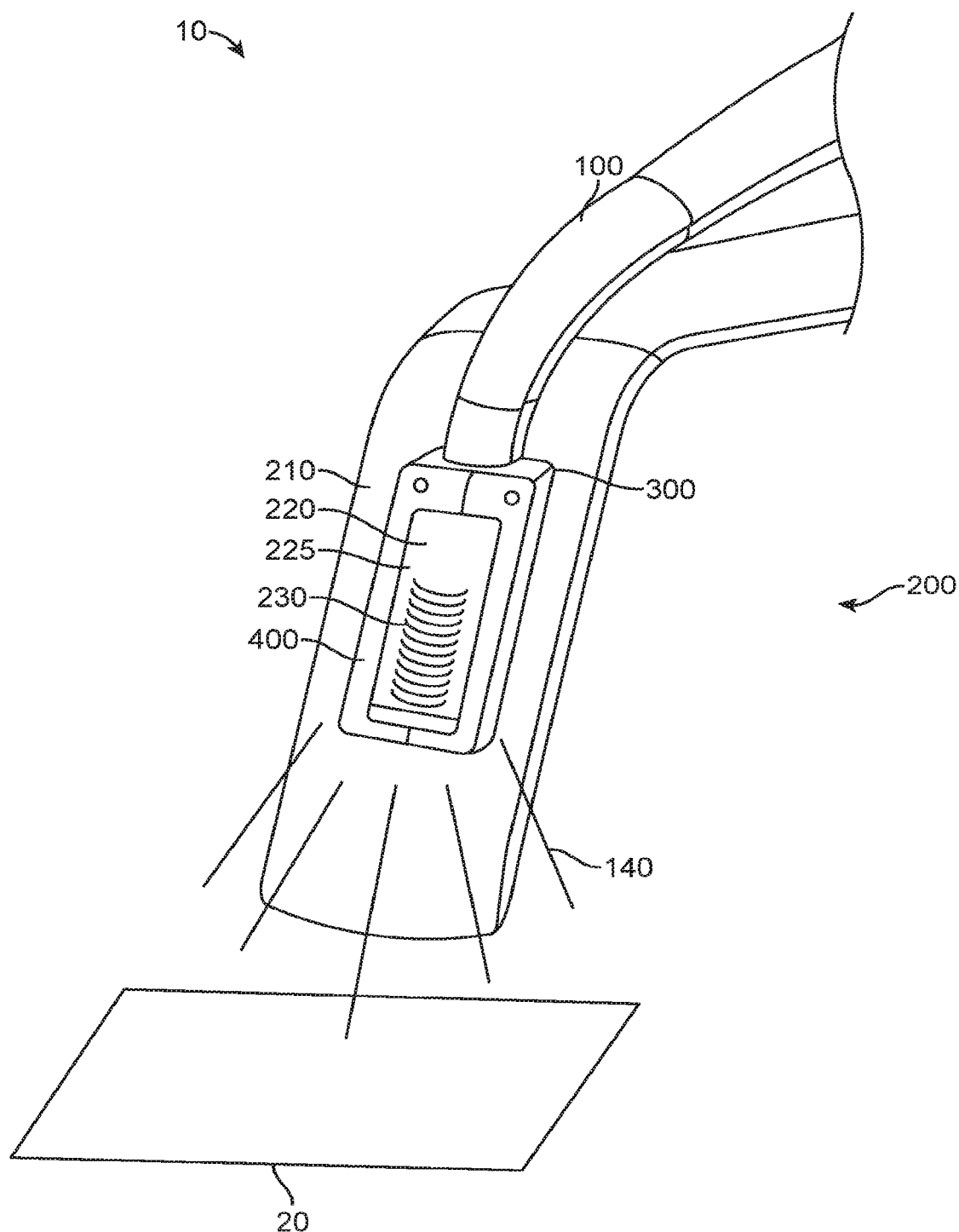
FIG. 1 shows a perspective view of an exemplary embodiment of an illuminated surgical apparatus.

FIG. 1 shows a perspective view of an exemplary embodiment of an illuminated surgical apparatus 10. The illuminated surgical apparatus comprises a fiber optic input 100, an illuminated surgical instrument 200, and an optical coupling bracket 300. The fiber optic input comprises one or more optical fibers. The illuminated surgical instrument comprises a surgical device 210 and an illumination element 220 coupled thereto. The optical coupling bracket receives and supports the fiber optic input, and couples the fiber optic input to the illumination element of the illuminated surgical instrument. The illumination element is configured to emit light 140 from the fiber optic input toward the surgical field 20. Additionally, the coupling bracket facilitates efficient coupling of the light input into the illumination element thereby reducing light loss and undesired heating.

In some embodiments, the illumination element comprises an optical waveguide 225 having one or more light emitting surfaces 230 adapted to face the surgical field. The light emitting surfaces may comprise a plurality of light extraction features such as facets, ridges, steps, or shoulders, or other geometries useful for extracting light from the waveguide and directing the light to the surgical field. In some embodiments, the illuminated surgical instrument further comprises an optional shroud 400 disposed around the optical waveguide, so as to protect the waveguide from damage and to provide additional structural integrity to the waveguide.

Figure 2:
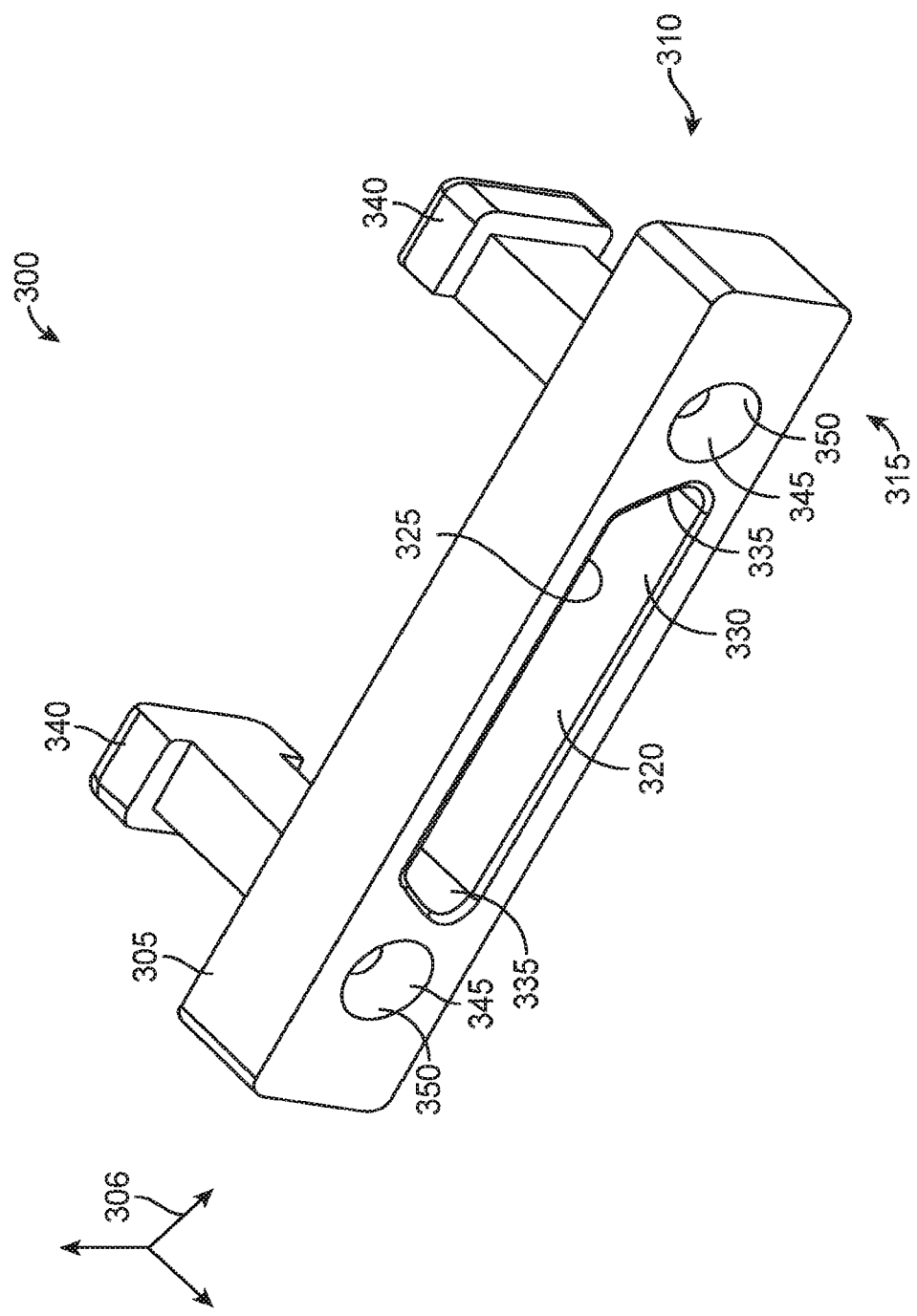
FIG. 2 shows a perspective view of an exemplary embodiment of an optical coupling bracket.

FIG. 2 shows a perspective view of an exemplary embodiment of an optical coupling bracket 300. The bracket comprises an elongate frame 305 having a proximal end 310, distal end 315, and a central channel 320 extending therebetween. The frame may comprise a rigid material, such as a metal or a rigid polymer, that can retain its structural integrity throughout its manufacturing process or its use in a surgical illumination apparatus. The central channel is defined by an upper surface 325, lower surface 330, and two side walls 335, and is sized to receive and support the light input element which in this embodiment is preferably one or more optical fibers of the fiber optic input. The proximal end can be coupled to the fiber optic input, and the distal end can be coupled to an illumination element configured to emit light from the fiber optic input.

The bracket may further comprise one or more protruding members (also referred to as legs) 340 disposed on the proximal end of the frame, adjacent to both side walls of the central channel, and extending in a direction transverse to the longitudinal axis 30 of the frame. In some embodiments, the protruding members 340 may extend perpendicularly to the longitudinal axis of the frame and in a proximal direction. The protruding members may comprise a rigid material similar to the material of the frame, and may be configured to flank the sides of the portion of the optical input extending past the proximal end of the frame, thereby providing further structural support to the optical input. The protruding members may be integrally formed with the frame or they may be separate components attached to the frame using methods known in the art.

The bracket may further comprise one or more engagement elements 345 disposed on the distal end of the frame, configured to engage the illumination element. The engagement elements may comprise one or more holes 350 configured to capture one or more of pins, screws, or protrusions disposed on and extending outward from a proximal surface of the illumination element, so as to fixedly or otherwise releasably engage the bracket to the illumination element.

Figure 3:
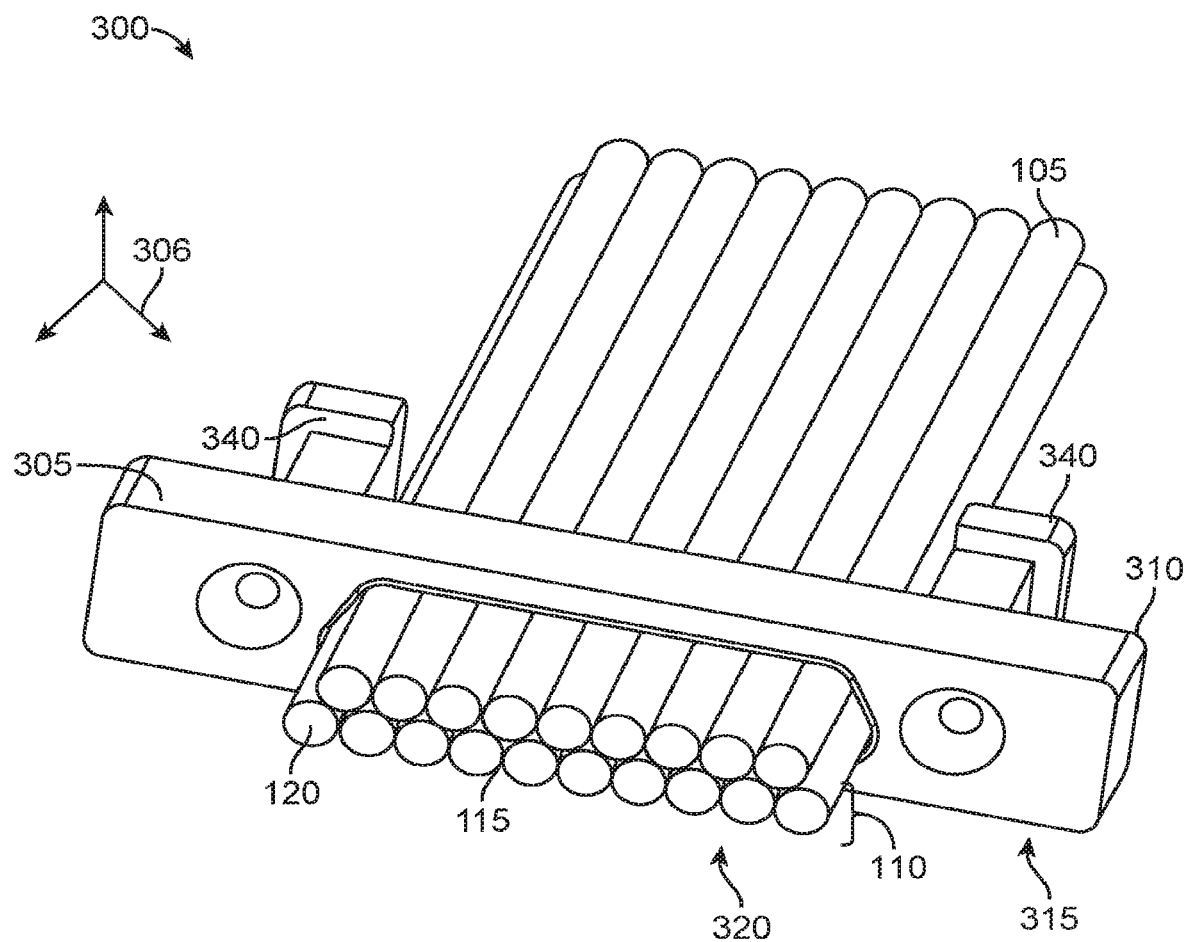
FIG. 3 shows a perspective view of an exemplary embodiment of an optical coupling bracket with captured optical fibers.

FIG. 3 shows a perspective view of an exemplary embodiment of an optical coupling bracket 300 with captured optical fibers 105. One or more optical fibers of the fiber optic input may be inserted into the central channel 320, optionally such that the distal tip 120 of the fibers extend past the distal end 315 of the frame 305. The fibers may be fixedly disposed in the channel by means of an adhesive 115. The optical fibers may be arranged in one or more linear arrays 110 that can be vertically stacked atop one another, such that the fibers can have a narrow profile that allows the bracket with the captured fibers to be coupled to a surgical device requiring a narrow profile for use. In some embodiments, the optical fibers are aligned in a configuration parallel to one or more protruding members 340 of the bracket, disposed as described herein. The protruding members may be configured to flank the sides of the portion of the optical fibers extending past the proximal end 310 of the frame, so as to provide additional structural support to protect the optical fibers against flexural loads and stresses at the proximal end of the frame. The fibers of one linear array may be offset from the fibers of an adjacent linear array such that the outer circumference of one or more fibers fits in a receptacle (also referred to as a trough) formed by adjacent fibers in an adjacent linear array.

The optical coupling bracket may also be used as a manufacturing fixture, providing a means to support optical fibers while the fibers undergo manufacturing processes such as trimming and polishing. Grasping the optical fibers without any intermediary structure may be difficult, and can subject the fibers to damage during the manufacturing processes. The bracket can facilitate the grasping and support of the fibers, and provide a structure that can interface with tooling fixtures while reducing the stresses placed on the fibers.

Figure 4:
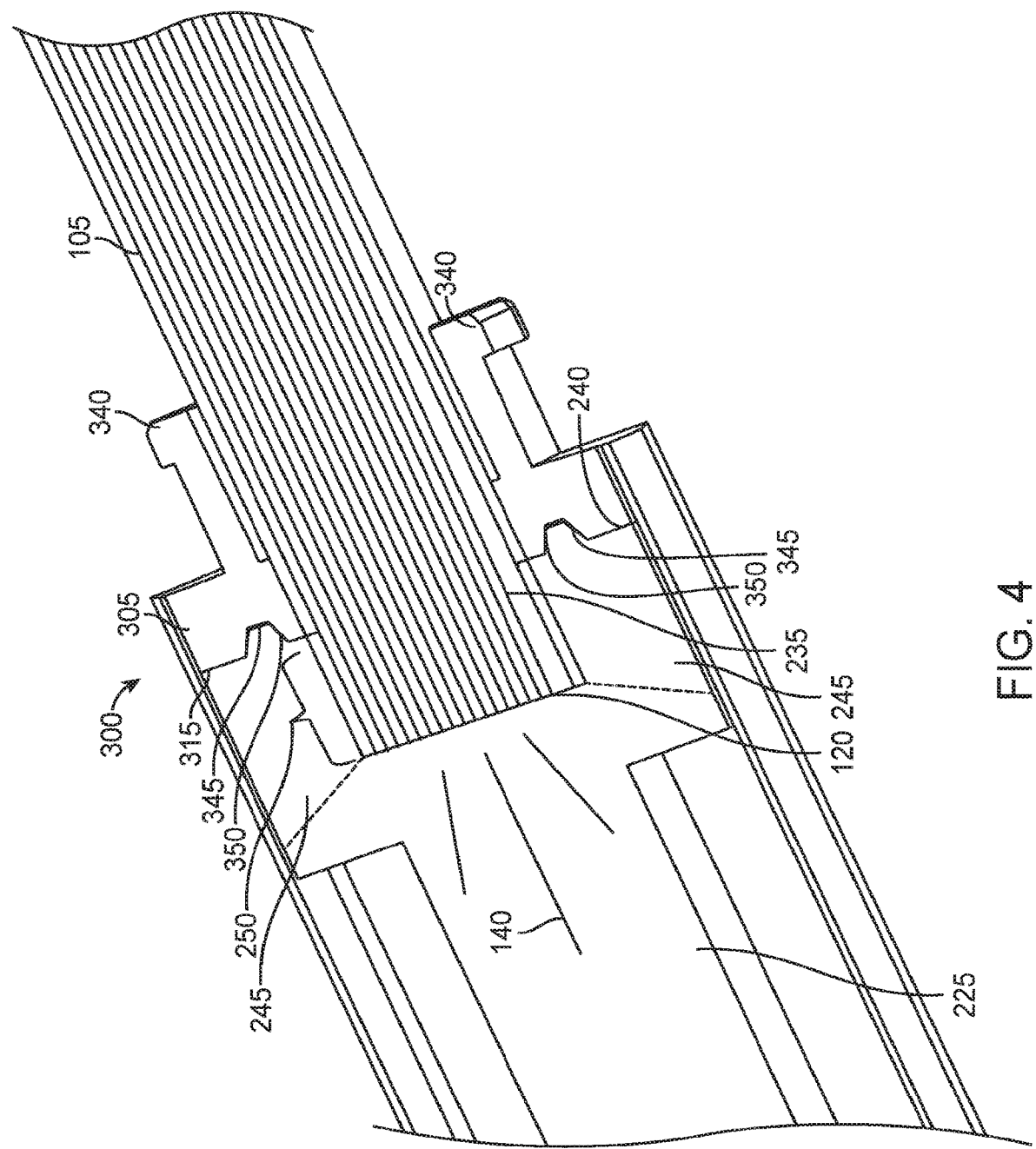
FIG. 4 shows a perspective view of an exemplary embodiment of an optical coupling bracket coupled to an optical waveguide.

FIG. 4 shows a perspective view of an exemplary embodiment of an optical coupling bracket 300 coupled to an optical waveguide 225. The optical waveguide may comprise a pocket 235 disposed on a proximal end 240 of the waveguide, which can be sized to receive the optical fibers 105 extending past the distal end 315 of the bracket frame 305. The bracket is coupled to the optical waveguide by engaging the distal end of the frame with the proximal end of the waveguide. The waveguide may be adhesively bonded to the distal end of the frame, or coupled to one or more engagement elements 345 disposed on the distal end of the frame. The engagement elements may comprise holes 350, and the waveguide may be coupled to the frame by means of pins or screws disposed in the holes. Alternately, the waveguide may comprise one or more protrusions disposed on the proximal end, and the protrusions may be disposed in the holes to attach the waveguide to the bracket frame. In alternative embodiments, adhesive may be used to bond the frame with the waveguide. In some embodiments, the frame and fibers may be fixedly attached to the waveguide, while in other embodiments, they are releasably coupled together.

The pocket of the waveguide can receive and support the distal end of the optical fibers, keeping the optical fibers together in a stable configuration, while providing a large bonding area between the optical fibers and the waveguide so as to enable the secure attachment of the fibers to the waveguide. The pocket can also provide a means to attach the fibers to the waveguide without interfering with light extraction from the waveguide. The pocket creates one or more dead zones 245 that lie outside of the light path, disposed between the proximal surface 240 of the waveguide and the distal tip 120 of the optical fibers. Since the dead zones lay proximal to the tip of fibers, they do not interfere with the propagation of light 140 from the fiber optic input, and the light can be transmitted past the dead zones to the light-emitting surfaces of the waveguide. Thus contact in the dead zones minimizes light loss and is a preferred location for engagement with adjacent components.

Coupling the optical fibers to the waveguide by means of the pocket can eliminate the need for an additional, external mechanical clasp feature, thereby keeping the profile of the waveguide as minimal as possible so as to enable the waveguide to be used in conjunction with a wide variety of surgical devices requiring a narrow profile. In addition, light extraction from the waveguide can be optimized without the use of an external mechanical clasp, since an external clasp can interfere with light extraction by potentially covering a portion of the external surface of the waveguide disposed in the path of light propagation thereby resulting in light loss in the contact area.

Preferably, the depth 250 of the pocket is about 3 mm or less, so as to maximize the area of the light-emitting surface of the optical waveguide and thereby optimize control over the light. A deeper pocket may further increase the area of the dead zones, which are outside of the path of light propagation and hence may not function as light-emitting surfaces. A deeper pocket may also pose additional challenges during the manufacturing of the optical waveguide. The interior surfaces of a deeper pocket may be difficult to polish sufficiently for the optimal transmission of light, and a deeper pocket may also require a larger draft angle to be used during the molding of the pocket, resulting in a less than ideal pocket configuration for securely holding the optical fibers.

In some embodiments, the optical coupling bracket 300 further comprises protruding members 340 as described herein, wherein the protruding members provide additional structural support to the optical fibers. The protruding members can serve to virtually extend the depth of the optical waveguide pocket, thereby providing further stability to the attachment of the optical fibers to the waveguide, without increasing the actual depth 250 of the pocket.

Figure 5A:
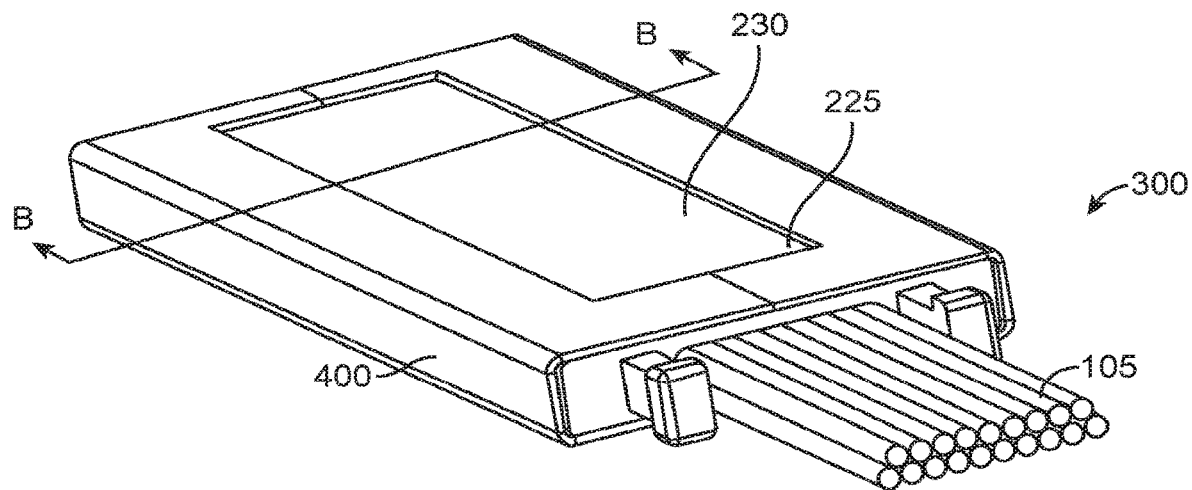
FIG. 5A shows a perspective view of an exemplary embodiment of an optical coupling bracket coupling optical fibers to an optical waveguide surrounded by a shroud.

FIG. 5A shows a perspective view of an exemplary embodiment of an optical coupling bracket 300 coupling optical fibers 105 to an optical waveguide 225 surrounded by an optional shroud 400. In some embodiments, the optical waveguide may be surrounded with a shroud in order to protect the waveguide from damage and to facilitate the handling of the waveguide. The shroud is disposed around at least a portion of a perimeter of the waveguide, and may comprise a rigid material similar to the material of the bracket. In some embodiments, both the shroud and the bracket are formed from a metal material, and the bracket may be fixedly coupled to the shroud by welding one or more surfaces of the bracket frame to one or more interior surfaces of the shroud.

Figure 5B:
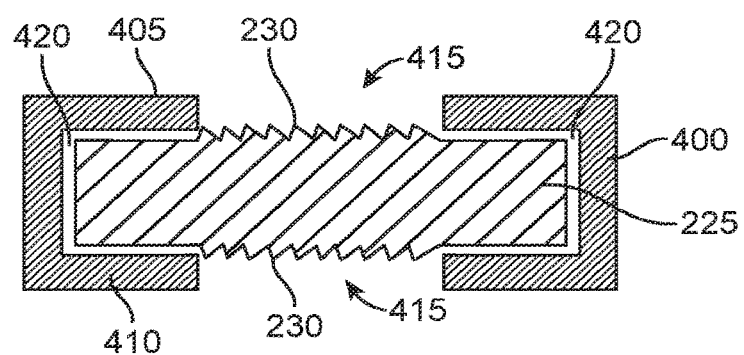
FIG. 5B shows a vertical cross-section of a shroud disposed around an optical waveguide.

FIG. 5B shows a vertical cross-section of a shroud 400 and disposed around an optical waveguide 225. The cross-section is taken along line B-B in FIG. 5A. The shroud comprises one or more openings 415 on a top surface 405, on a bottom surface 410, or on both the top surface and the bottom surface of the shroud. The openings are configured to allow the light-emitting surfaces 230 of the waveguide to emit light from the fiber optic input toward the surgical field, wherein the light-emitting surfaces may be disposed on one or more of a top surface, a bottom surface, or a distal tip of the waveguide. Preferably, the shroud is configured to maintain an air gap 420 between the waveguide and one or more interior surfaces of the shroud, so as to minimize the degree to which the shroud may interfere with light propagation through the waveguide because light loss may occur at points of contact with the waveguide.

Figure 6:
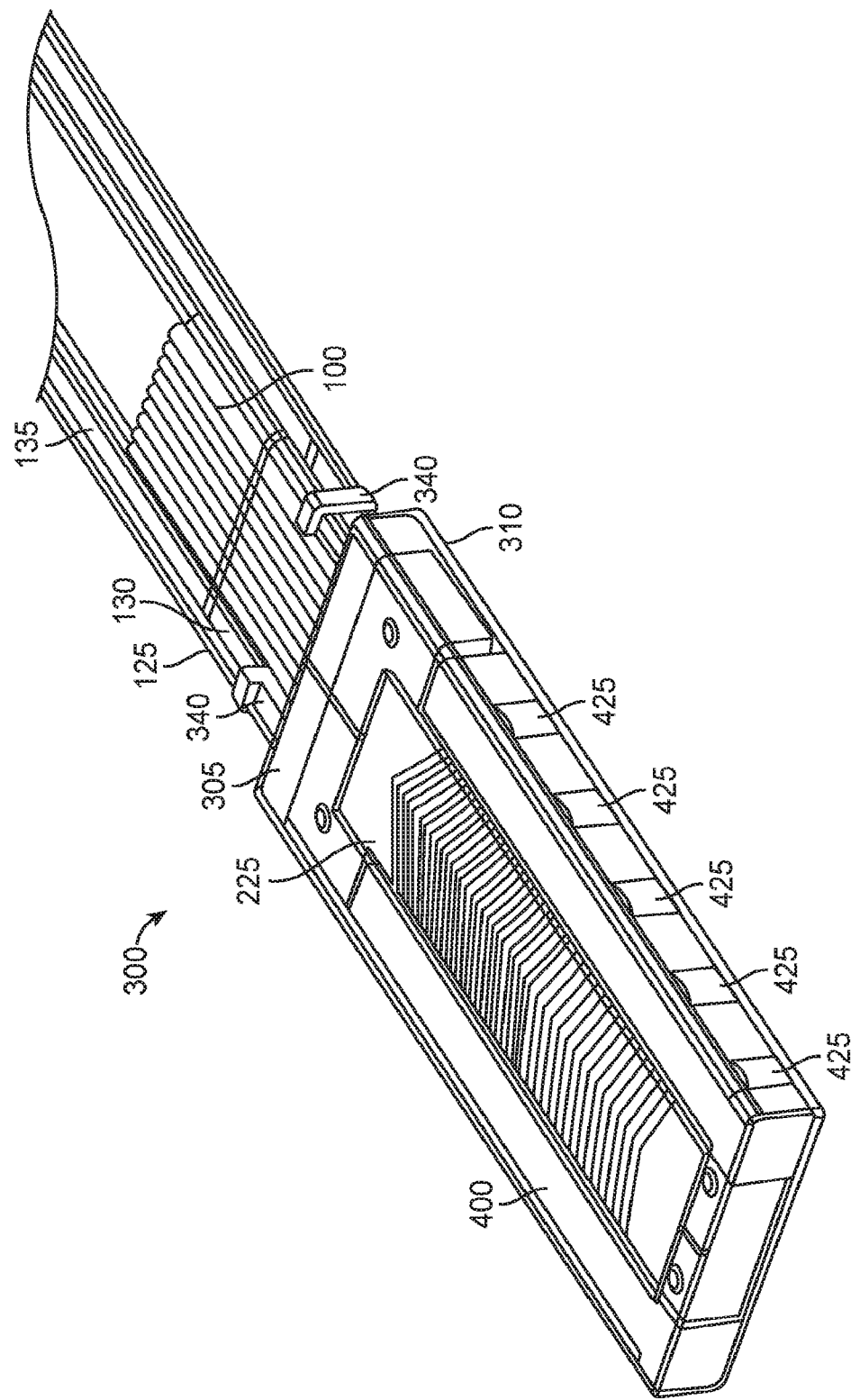
FIG. 6 shows a perspective view of an exemplary embodiment of an optical coupling bracket coupling a fiber optic input to an optical waveguide surrounded by a shroud.

FIG. 6 shows a perspective view of an exemplary embodiment of an optical coupling bracket 300 coupling an fiber optic input 100 to an optical waveguide 225 surrounded by a shroud 400. The fiber optic input, bracket, and waveguide may be coupled together as described herein. The proximal portion of the fiber optic input, extending past the proximal end 310 of the bracket frame 305, may form a short, structurally reinforced section referred to as a pigtail 125. The pigtail may comprise the proximal portion of the optical fibers disposed between the protruding members 340, as described herein, and optionally a band 130 disposed around the protruding members. The band such as a heat shrink wrap, optical cladding or any other cover, can help to couple the optical fibers and the bracket in a stable configuration, and reduce the flexural loads and stresses at the proximal connection between the optical fibers and the bracket. The pigtail can further connect to a cable or ribbon 135 that optically couples the pigtail to the light source of the fiber optic input.

In some embodiments, the shroud 400 further comprises one or more magnets 425 configured to magnetically couple the shroud with a surgical device. The magnets may be integrated with or coupled to one or more surfaces of the shroud. The magnetic coupling of the shroud to the surgical device can provide additional support to the distal end of the optical waveguide, so as to prevent the distal end of the waveguide from flipping up away from the surface of the surgical device. The magnets are of suitable strength so that the shroud is secured to the surgical device and unwanted movement is prevented during the surgical procedure. Additionally, the magnet strength may be selected to allow easy attachment and detachment of the shroud from the surgical device, thereby allowing repositioning. In some circumstances, the surgical device may not be magnetic, and thus tape strips of ferrous metal or other magnetic materials may be applied to the surgical device so that the shroud may be magnetically coupled thereto.

Figure 7:
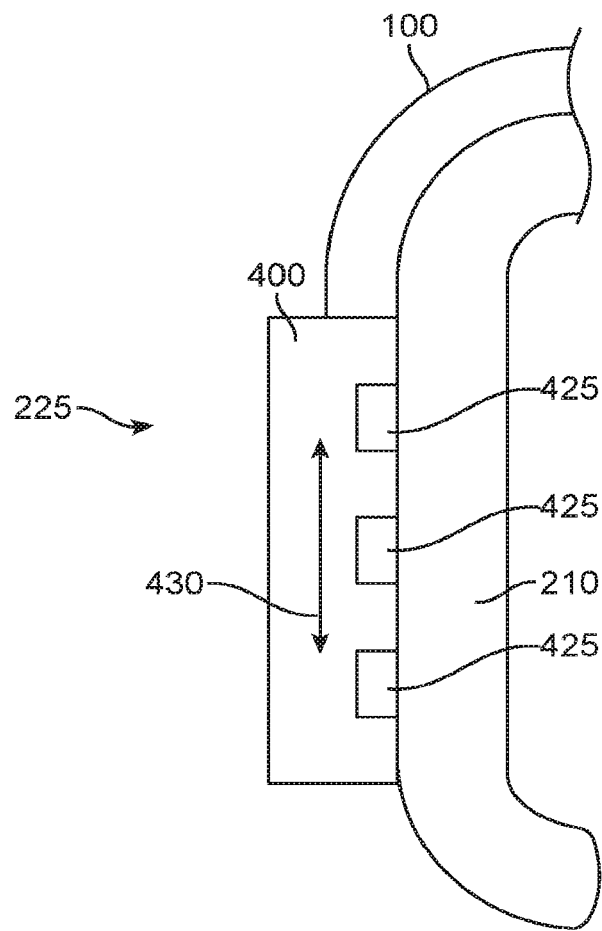
FIG. 7 shows a side view of an exemplary embodiment of magnetic coupling of a shroud disposed around an optical waveguide to a surgical device.

FIG. 7 shows a side view of an exemplary embodiment of the magnetic coupling of a shroud 400 disposed around an optical waveguide 225 to a surgical device 210. One or more small, discrete magnets 425 are integrated into the shroud, and the magnets couple the shroud and the optical waveguide disposed within the shroud to a magnetic surface of the surgical device. The magnets may be configured to be moveable within the shroud, for example up and down the length of the shroud in the direction of the arrow 430, such that the shroud may be adapted to attach to a curved surface of a surgical device.

Alternately to having magnets coupled to the shroud, the magnets may also be integrated with or coupled to one or more surfaces of the surgical device, such that a shroud comprising a magnetic material may be magnetically coupled thereto.

The various features disclosed herein may be mixed, matched, or substituted with one another. Thus, for example, any of optical coupling bracket embodiments may be combined with any additional structural feature disclosed herein, such as the shroud. Any of the features disclosed in this application may also be used in conjunction with or substituted with any of the features disclosed in the patents and applications incorporated herein by reference.

Figure 8A:
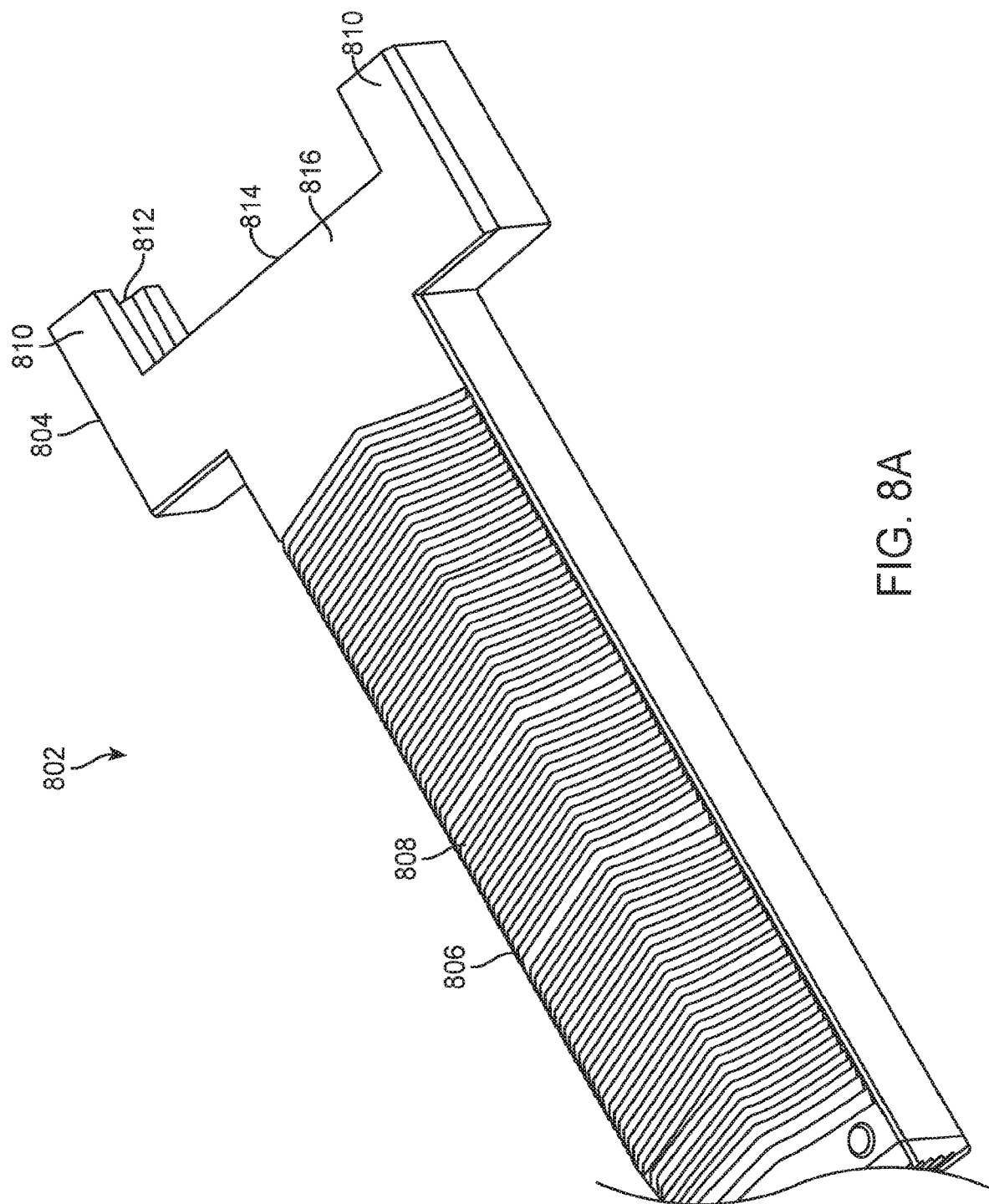
FIG. 8A shows a perspective view of an alternative embodiment of an illumination element.
Figure 8B:
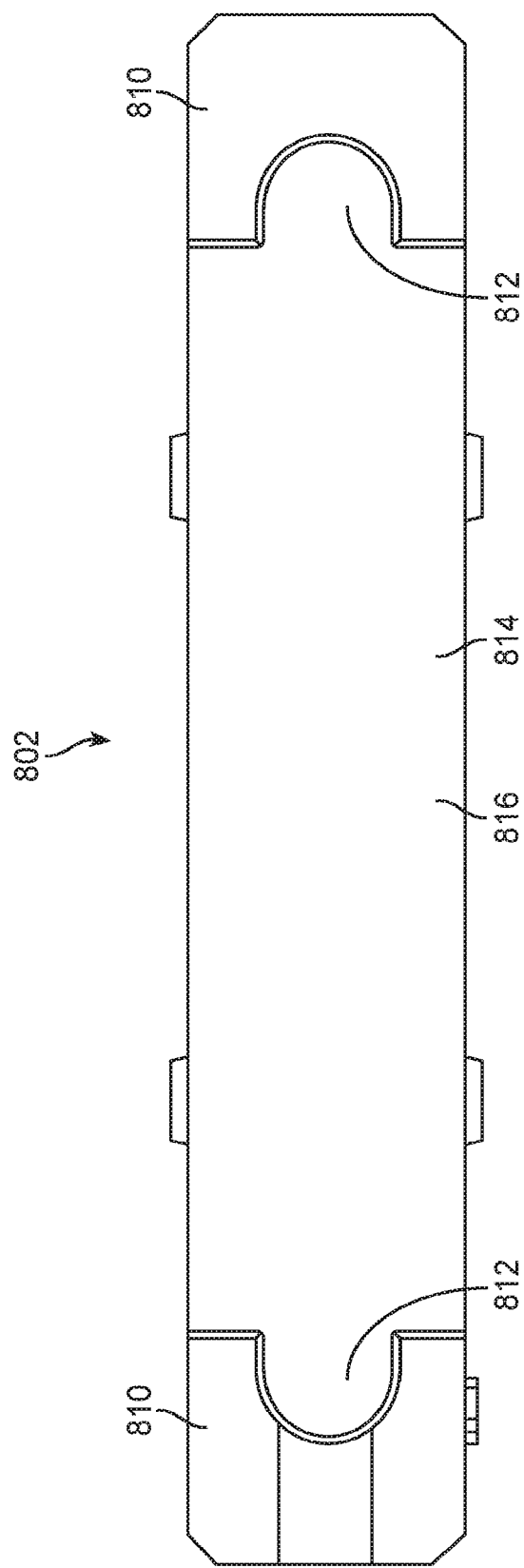
FIG. 8B shows an end view of FIG. 8A.

FIGS. 8A-8B show an alternative embodiment of an illumination element 802. The illumination element 802 has a distal portion 806 and a proximal portion 804. A plurality of optical structures 808 are disposed along the distal portion of the illumination element and they are shaped to help efficiently transmit light from the proximal portion to the distal portion of the illumination element. The plurality of optical structures 808 are also shaped to facilitate extraction of light from the illumination element and to direct the extracted light toward a target work area such as a surgical field. The proximal portion includes two legs 810 on either lateral side of the illumination element. A proximal-most end 816 of the illumination element and the two legs 810 define a pocket or receptacle 814 that is sized to receive an illumination element as described below. A keyway element 812 which in this embodiment may be a channel extending along the longitudinal axis of one or both legs is sized to receive a correspondingly shaped keyway element on a light input element or a coupling bracket to ensure proper alignment and orientation of the illumination element with the input element or coupling bracket as will be discussed in greater detail below. The illumination element is preferably a non-fiber optic optical waveguide and the light is preferably transmitted therethrough via total internal reflection. The optical structures may be any optical structure disclosed in this specification or in any of the references incorporated by reference, or otherwise known in the art, and may include optical structures such as lenses, facets, prisms, etc. In preferred embodiments the optical structures are stair steps having a ramp surface and a step surface. The ramp is preferably angled to promote total internal reflection of light within the optical waveguide, and the step is preferably angled to extract the light from the illumination element and direct the extracted light to the target work area such as a surgical field. An angle may be disposed between the ramp and step surfaces. This angle may be constant along the optical structures, or this angle may change from stair step to stair step. The distal-most face or surface of the illumination element may also have optical structures for extracting and controlling the light as will be described in greater detail below. The legs 810 provide dead zones where light does not pass or substantially no light passes, therefore the legs form ideal locations for engagement with the light input or coupling bracket, thereby minimizing light loss due to contact between the input and the illumination element. FIG. 8B illustrates an end view of the illumination element, highlighting the proximal end thereof. The keyway elements in this exemplary embodiment are D-shaped channels extending through both legs, although one of skill in the art will appreciate that many other shapes are possible and this is not intended to be limiting.

FIGS. 9A-9D show an exemplary coupling bracket 902 that may be fitted with the illumination element in FIGS. 8A-8B above and helps couple a light input element with the illumination element. The coupling bracket 902 has a proximal portion 904 and a distal portion 906. A central channel 908 extends through the bracket from the proximal portion to the distal portion. A keyway element 910 is disposed on one or both lateral sides of the coupling bracket and has a shape that corresponds with the keyway element 812 on the illumination element 802 so that the two keyway elements slidably engage one another and ensure proper alignment and orientation of the illumination element 802 with the coupling bracket 902. In this exemplary embodiment, the keyway element 910 is preferably a protrusion on both sides of the coupling bracket and the protrusion has a D-shaped cross-section sized to fit into the D-shaped channel 812 on the illumination element. Additionally, wings 912 may also be provided on one or both lateral sides of the coupling bracket to provide additional surfaces that help align and engage the coupling bracket with the illumination element when the coupling bracket is received in the receptacle in the illumination element. Additional alignment elements such as rectangular tabs 914, 920 may extend outward from the wings 912 to also provide alignment and engagement surfaces for mating with the illumination element, or an instrument such as a retractor or other surgical instrument which may be coupled with the illumination element. Tab 914 is preferably an elongate rectangular shaped protrusion having a longitudinal axis which is generally parallel with the longitudinal axis of the coupling bracket or the central channel. Coupling bracket is also a preferably an elongate rectangular shaped protrusion but it is oriented transversely relative to tab 914 such that the longitudinal axis of tab 920 is transverse or orthogonal to the longitudinal axis of the coupling bracket or central channel. A distal face 916 of either wing 912 is preferably a flat planar surface to allow the coupling bracket to butt firmly and evenly against the illumination element. Similarly, the distal-most face 918 of the coupling bracket is also preferably a flat planar surface to further facilitate firm and even engagement of the coupling bracket against a surface of the illumination element when disposed therein. The proximal portion of the coupling bracket may be any shape, but in this embodiment has a slightly proximally facing taper to ensure a smooth transition with the illumination element when the illumination element is coupled therewith. The distal portion of the coupling bracket may also be any shape, but in this exemplary embodiment is preferably rectangular shaped. The central channel 908 is preferably parallelogram shaped with parallel upper and lower walls, and inwardly canted side walls.

Figure 9A:
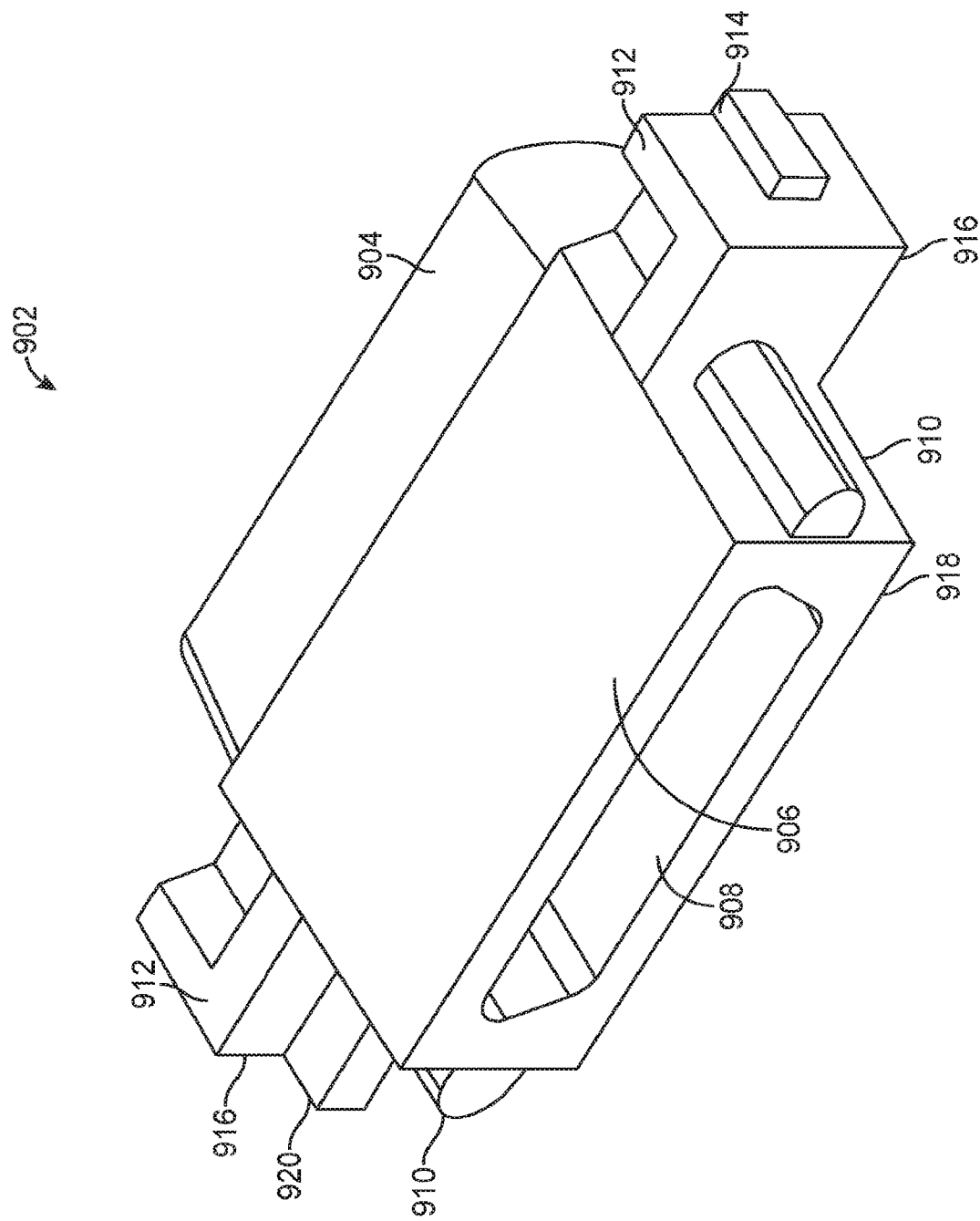
FIG. 9A shows a perspective view of an exemplary embodiment of a coupling bracket.
Figure 9B:
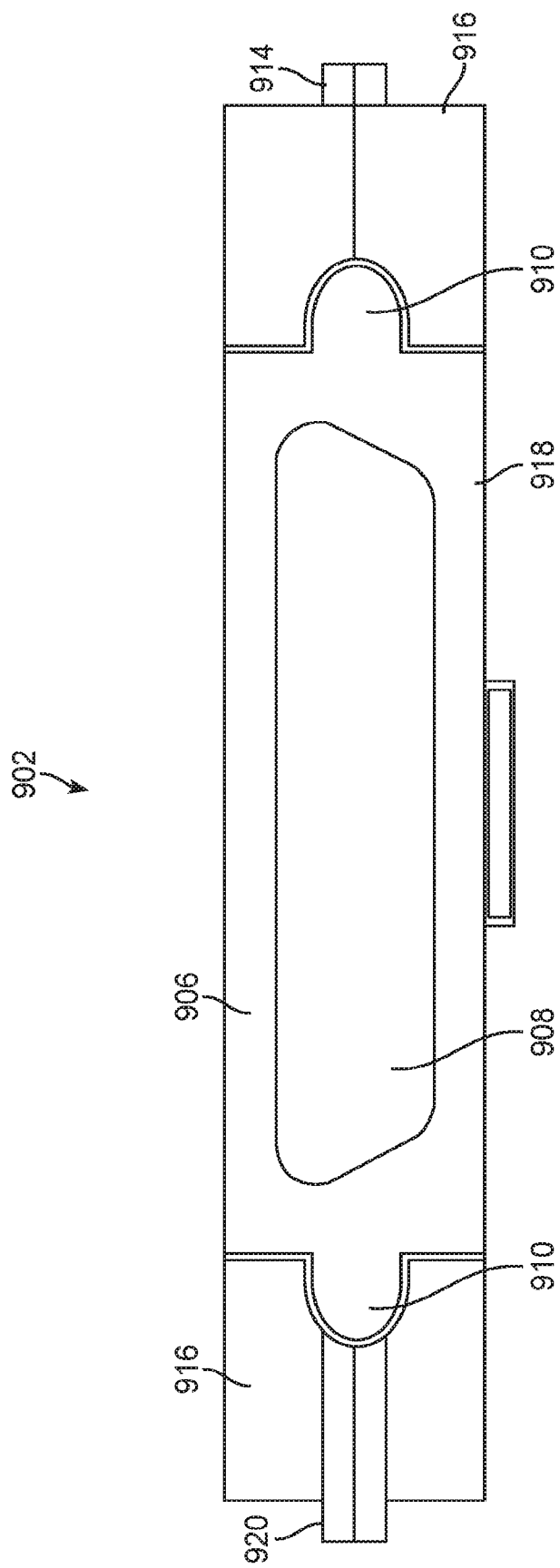
FIG. 9B shows an end view of FIG. 9A.
Figure 9C:
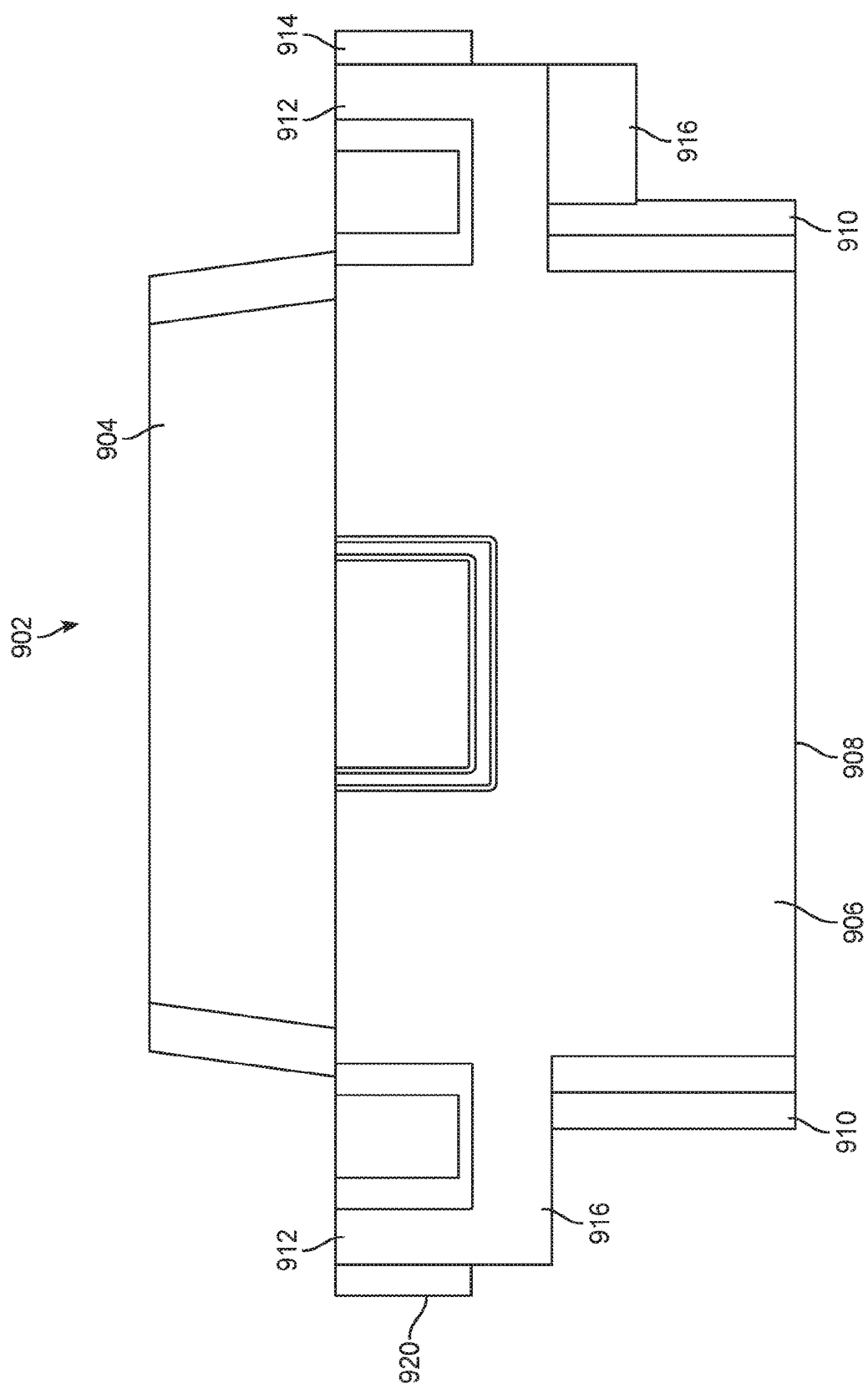
FIG. 9C shows a top view of FIG. 9A.
Figure 9D:
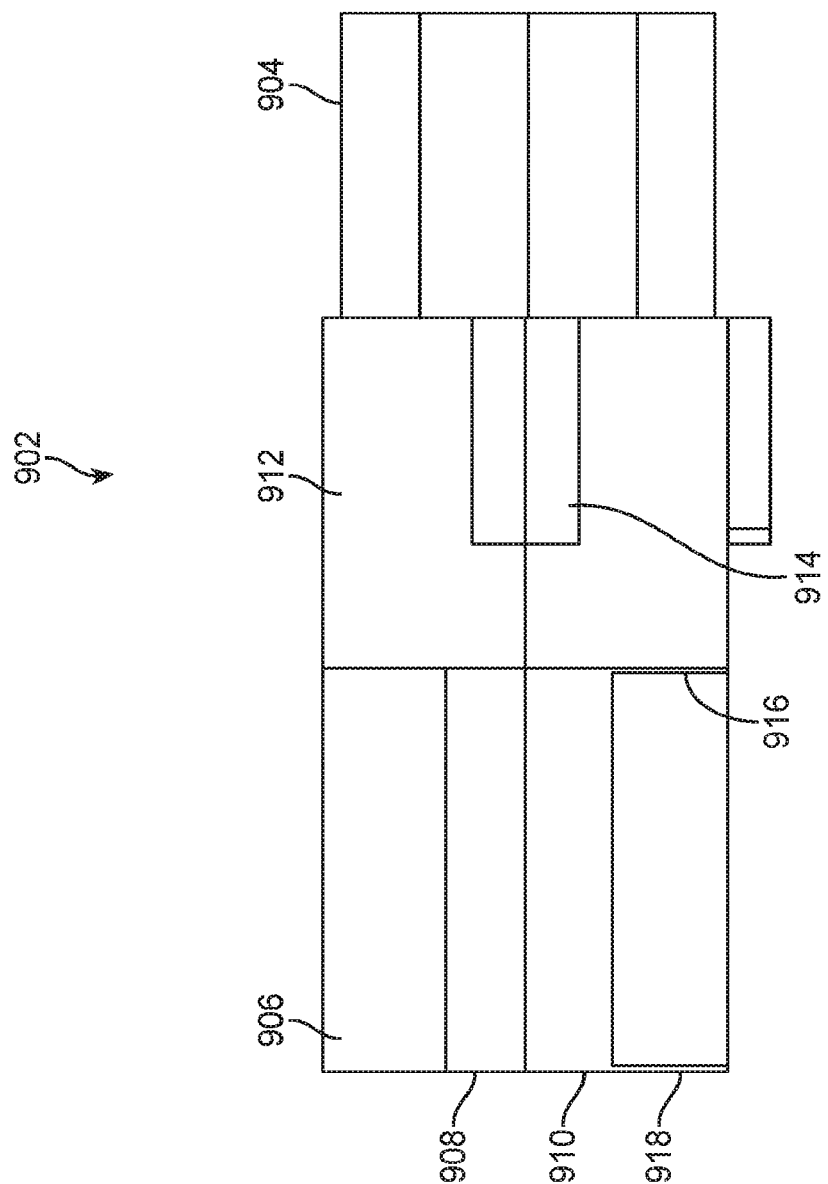
FIG. 9D shows a side view of FIG. 9A.

FIG. 9B shows an end view of the coupling bracket and highlights the central channel 908. The central channel is sized to receive a light input element which in preferred embodiments is one or more fiber optics. When the light input element includes a plurality of fiber optics, the individual optical fibers may be aligned and stacked as one or more linear arrays of fibers stacked on top of one another as will be illustrated later. FIG. 9C illustrates a top view of the coupling bracket 902 and FIG. 9D shows a side view of the coupling bracket 902.

Figure 10A:
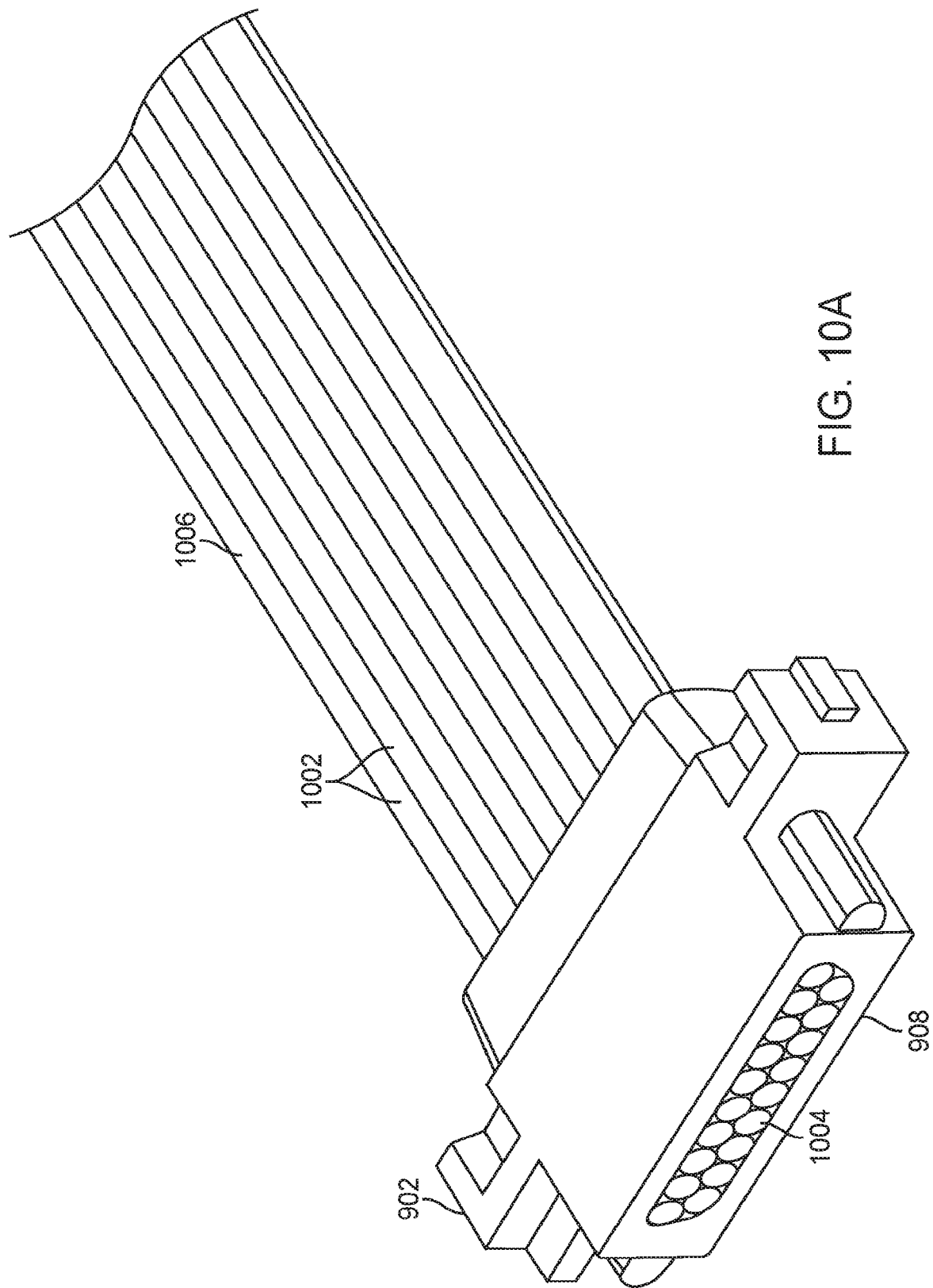
FIG. 10A shows a perspective view of a plurality of optical fibers disposed in the coupling bracket of FIG. 9A.

FIG. 10A shows a perspective view of the coupling bracket 902 described above with a light input element 1006 disposed in the central channel 908. In this embodiment, the light input element comprises a plurality of optical fibers that are arranged in two rows of fibers stacked on top of one another. The fibers 1002 are aligned in two linear arrays with the two arrays slightly staggered or offset from one another so that the bottom portion of an upper fiber fits in a trough formed by two adjacent fibers on the bottom. Similarly, a top portion of a lower fiber fits in the trough formed by two adjacent fibers on a top row. This helps maximize fiber packing and minimizes profile. Each fiber in a linear array is adjacent another fiber so that their outer circumferences engage one another. Additionally, the distal-most faces 1004 of the fibers are preferably aligned with the distal-most end of the coupling bracket forming a smooth, flat and flush distal end that can be butted against the illumination element when the assembly of the coupling bracket and optical fibers are disposed in the receptacle. Just as previously disclosed, the coupling bracket may also be used during manufacturing as a process aid to help fixture the fibers so that they can be polished and otherwise processed.

Figure 10B:
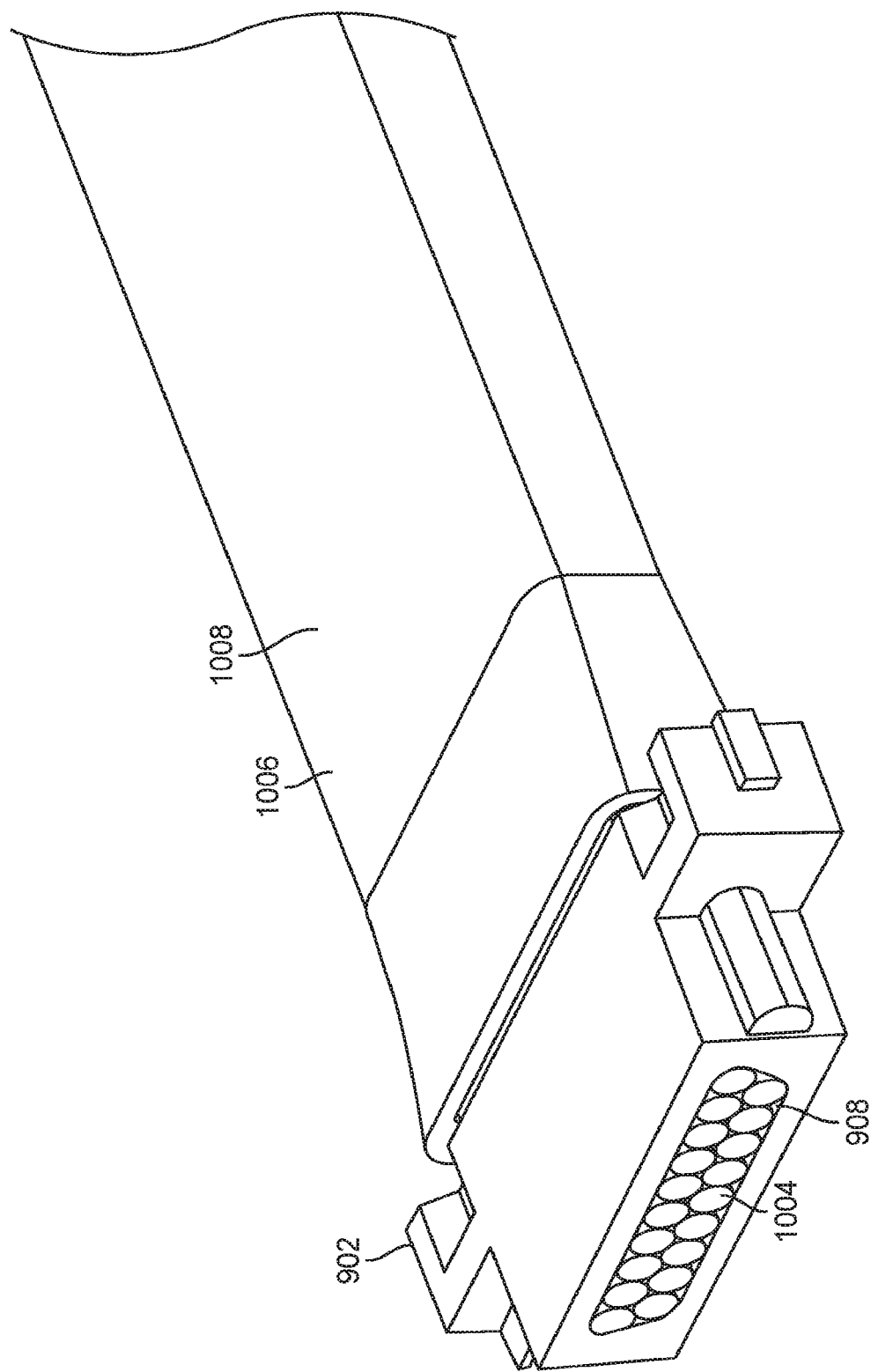
FIG. 10B shows a perspective view of FIG. 10A with an outer cover disposed over the optical fibers.

FIG. 10B shows an alternative embodiment of FIG. 10A, where an outer cover or sheath 1008 may be disposed over the light input element 1006 which includes optical fibers 1002. The sheath may be heat shrink, an optical cladding, or another other cover to help protect the fibers, or to provide desired optical properties to the fiber bundle, or the help keep the fibers shaped into a ribbon.

Figure 11:
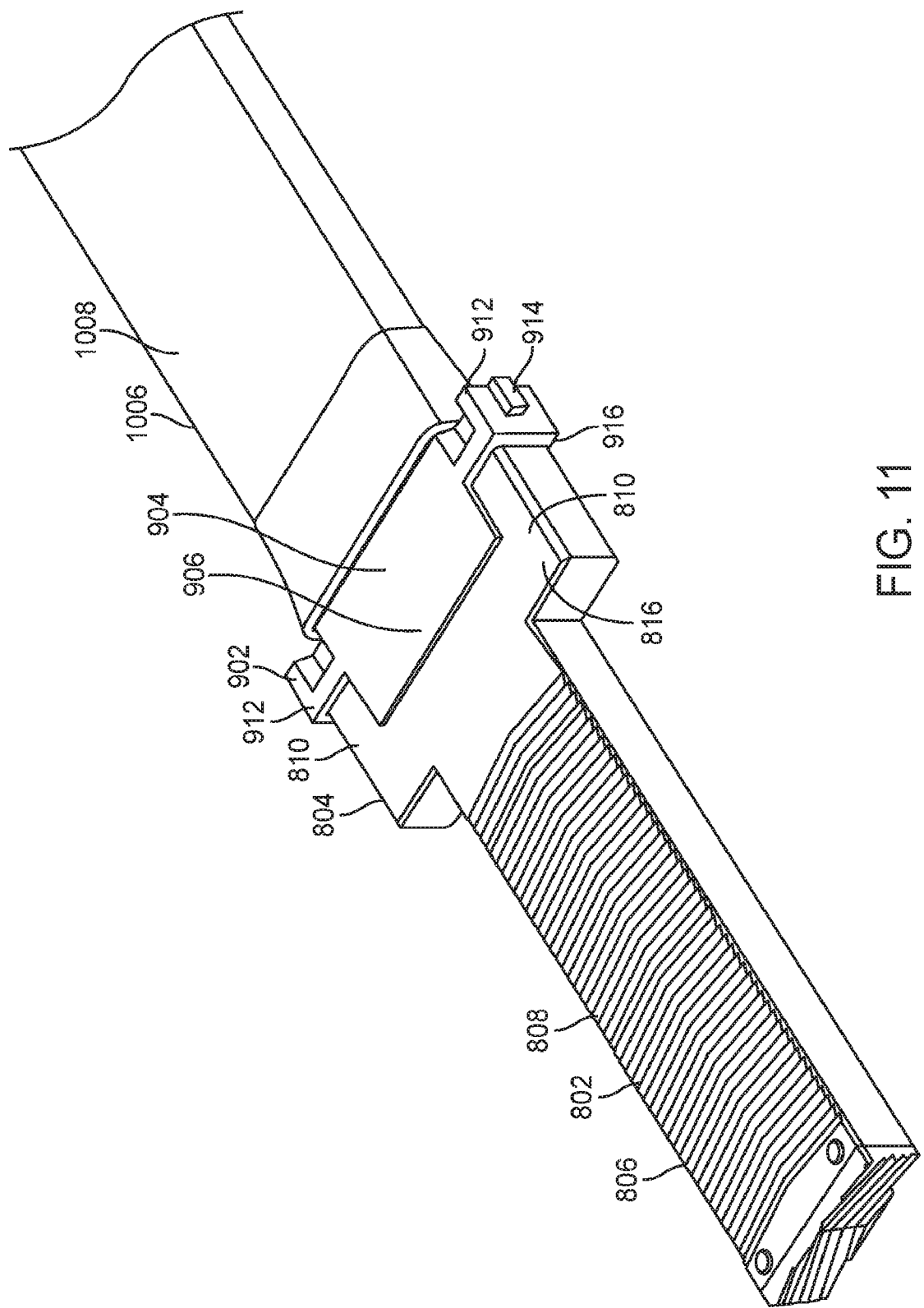
FIG. 11 shows a perspective view of an exemplary embodiment of an assembly comprising the illumination element of FIG. 8A, the coupling bracket of FIG. 9A, and a light input element which includes optical fibers in the coupling bracket and an outer cover disposed over the optical fibers.

FIG. 11 shows an exemplary embodiment of an assembly comprising the illumination element 802 with the coupling bracket 902 and the light input element 1006 covered by the outer cover 1008. The assembly may then be fixedly or removably coupled to a tool or instrument such as a surgical retractor blade to help illuminate a surgical field. Any instrument may be coupled to the assembly in order to illuminate the work area. Preferred embodiments utilize a surgical instrument or medical device such as a suction tube, an electrosurgical instrument, a camera, a sensor, or any other instrument or tool. In the assembly of FIG. 11, the assembly may be coupled together fixedly or releasably. For example, adhesive may be used to bond the assembly together. The adhesive may be an optical adhesive having desired index matching properties to ensure efficient transmission of light from the light input element to the illumination element. In other embodiments, the assembly may be snap fit together, snap fit or threadably engaged with one another, or any other coupling means may be used to join the components together. FIG. 11 also highlights the distal-most end of the illumination element which may have optical structures for extracting and directing light to the work area such as a surgical field. Other aspects such as a shroud, magnetic coupling, or any other features previously described may be combined with or substituted for features of the present embodiment.

FIGS. 12A-12C show a perspective view of an alternative embodiment of an illumination element 1300 and a coupling bracket 1200. The illumination element may comprise an optical waveguide 1300 having a distal end 1310 and a proximal end 1320. The optical waveguide 1300 may further comprise a pocket 1330 disposed on the proximal end 1320 and the pocket 1330 may be configured to receive at least the distal end 1210 of the coupling bracket 1200. The coupling bracket 1200 may further comprise a protrusion 1205 and/or a receptacle 1215, and the waveguide 1300 may comprise a matching receptacle 1305 and/or matching protrusion 1315. The protrusions 1205 and 1315 may be configured to snap fit into the receptacles 1305 and 1215 to couple the bracket to the illumination element. The waveguide 1300 may further comprise a protrusion 1325 that extends partially or completely as shown on the sides of the waveguide, configured to slide into a matching receptacle on a surgical instrument (not shown). FIG. 12B shows how the bracket 1200 may be inserted vertically into the pocket 1330 of the waveguide 1300. FIG. 12C shows how the bracket may be disposed in the pocket 1330 of the waveguide 1300 and also shows how the bracket may be coupled to the waveguide 1300 by snap fitting the protrusions 1205 and 1315 into the receptacles 1305 and 1215.

Coupling the bracket to the waveguide by means of the pocket can eliminate the need for an additional, external mechanical clasp feature, thereby keeping the profile of the waveguide as minimal as possible so as to enable the waveguide to be used in conjunction with a wide variety of surgical devices requiring a narrow profile. In addition, light extraction from the waveguide can be optimized without the use of an external mechanical clasp, since an external clasp can interfere with light extraction by potentially covering a portion of the external surface of the waveguide disposed in the path of light propagation thereby resulting in light loss in the contact area.

Figure 13A:
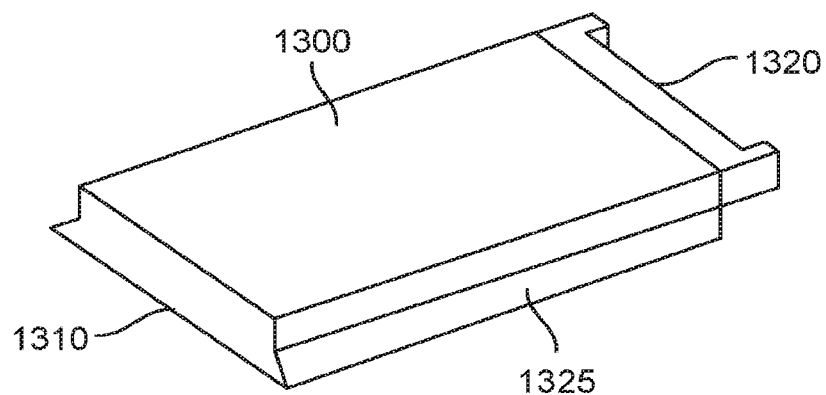
FIG. 13A shows a perspective view of an alternative embodiment of an illumination element.

FIG. 13A shows a perspective view of an alternative embodiment of an illumination element 1300 that may be used with any of the embodiments described herein. The illumination element may comprise an optical waveguide 1300 that may comprise a protrusion 1325 configured to slide into a matching receptacle on a surgical instrument (not shown). The optical waveguide 1300 or the surgical instrument may comprise a protrusion and the other of the waveguide or the surgical instrument may comprise a matching receptacle. The protrusion may be configured to slide into the receptacle to couple the waveguide to the instrument. The protrusion may be any shape such as a dovetail or other shape and it may extend partially or completely along one or both sides of the waveguide.

Figure 13B:
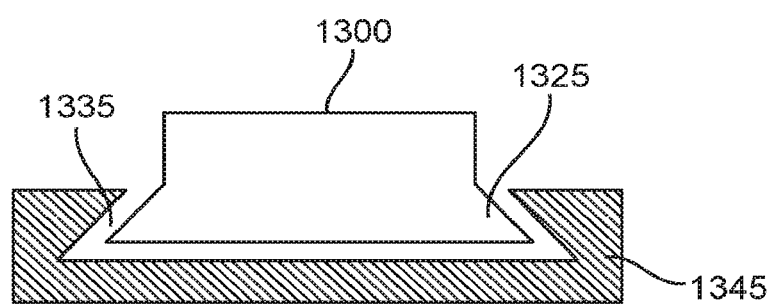
FIG. 13B shows an end view of the illumination element from FIG. 13A engaged with a surgical instrument.

FIG. 13B shows an end view of the embodiment of FIG. 13A. The protrusion 1325 on the waveguide 1300 may be slid into a matching receptacle 1335 on a surgical instrument 1345 such as a retractor blade, or any other surgical instrument described herein. FIG. 13B further shows that the protrusion 1325 may have a dovetail-shape and the matching receptacle 1335 may be a dovetail-shaped groove.

Figure 14A:
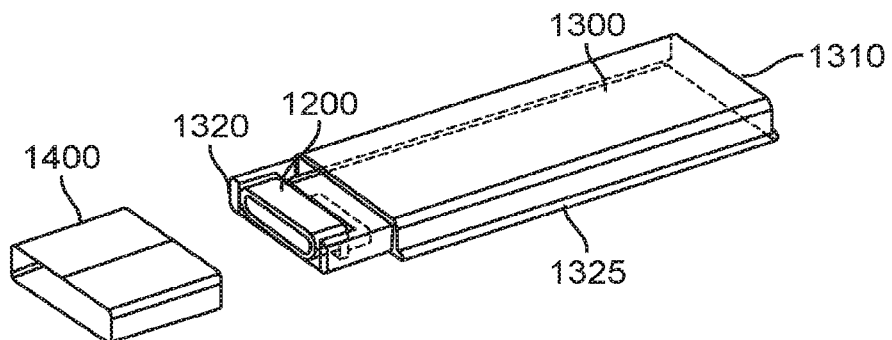
FIG. 14A shows a perspective view of the embodiment of FIG. 12C and a collar.

FIG. 14A shows a perspective view of the embodiment of FIG. 12C and a collar 1400 configured to be disposed over at least a portion of the illumination element 300, at least a portion of the fiber optic input (not shown), and the coupling bracket 1200. The illumination element may comprise an optical waveguide 1300. One of the collar 1400 or the coupling bracket 1200 may comprise a protrusion, and the other of the collar or the coupling bracket may comprise a receptacle. The protrusion may be configured to snap fit into the receptacle to couple the collar 1400 to the coupling bracket 1200. The collar may comprise a rectangular, square or other geometrically shaped tube. The tube may define a central channel sized to receive, protect, support, or secure the coupling interface between any of the illumination element 300, the coupling bracket 1200, and the fiber optic input. The collar may also provide strain relief for the various components of the apparatus or device.

Figure 14B:
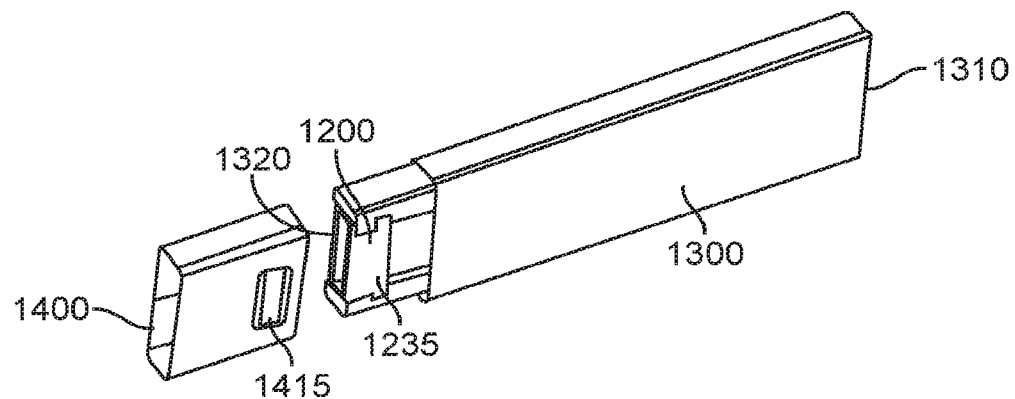
FIG. 14B shows a bottom perspective view of the embodiment of FIG. 14A.

FIG. 14B shows an alternative perspective view of the embodiment of FIG. 12C and the collar 1400 of FIG. 14A. The collar 1400 may comprise a receptacle 1415 and the coupling bracket 1200 may comprise a protrusion 1235. The protrusion 1235 may be configured to snap fit into the receptacle 1415 to couple the collar 1400 to the coupling bracket 1200 as the collar 1400 is moved axially over the coupling bracket 1200.

Figure 14C:
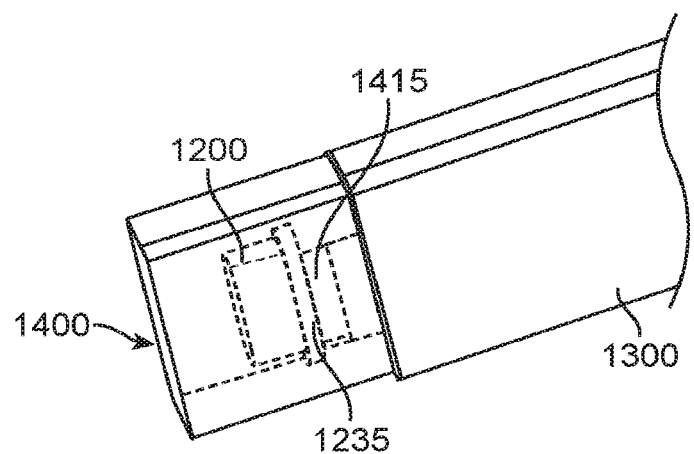
FIG. 14C shows the collar of FIGS. 14A-14B disposed over the illumination element.

FIG. 14C shows the collar 1400 of FIG. 14B disposed over at least a portion of the embodiment of FIG. 12C. The coupling bracket 1200 may comprise a protrusion 1235, which may be snap fit into a receptacle 1415 on the collar 1400 to couple the collar 1400 to the coupling bracket 1200 as shown in FIG. 14C.

Figure 15A:
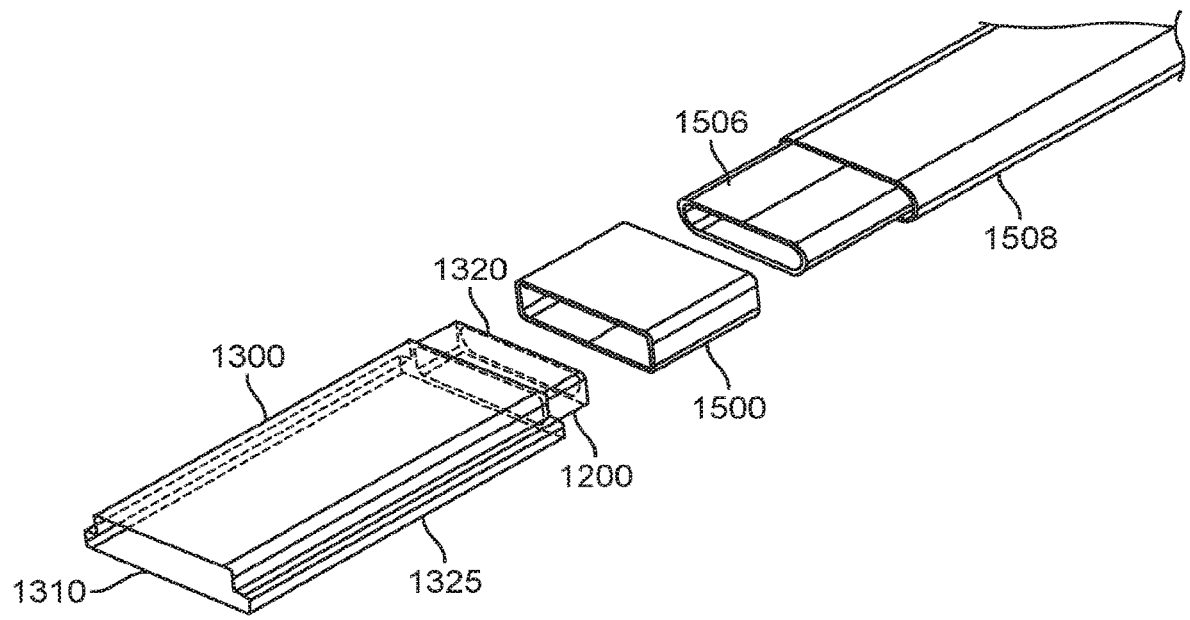
FIG. 15A shows a perspective view of an alternative embodiment of an illumination element, a coupling bracket, a fiber optic input, and a collar.

FIG. 15A shows a perspective view of an alternative embodiment of an illumination element 1300, a coupling bracket 1200, light input element 1506, and a collar 1500, configured to be disposed over the illumination element 1300, the coupling bracket 1200, and the light input element 1506. The illumination element may preferably comprise an optical waveguide 1300, and the light input element may preferably comprise a fiber optic input 1506. The collar 1500 may be configured to slide over at least a portion of the optical waveguide 1300 and the coupling bracket 1200. The collar 1500 may be adhesively coupled or otherwise adhered to at least one of the coupling bracket 1200, the fiber optic input 1506, or the optical waveguide 1300. Methods for adhesion may comprise press-fitting, crimping, welding, and other methods known in the field. At least a portion of the fiber optic input 1506 may be disposed in a cover 1508.

Figure 15B:
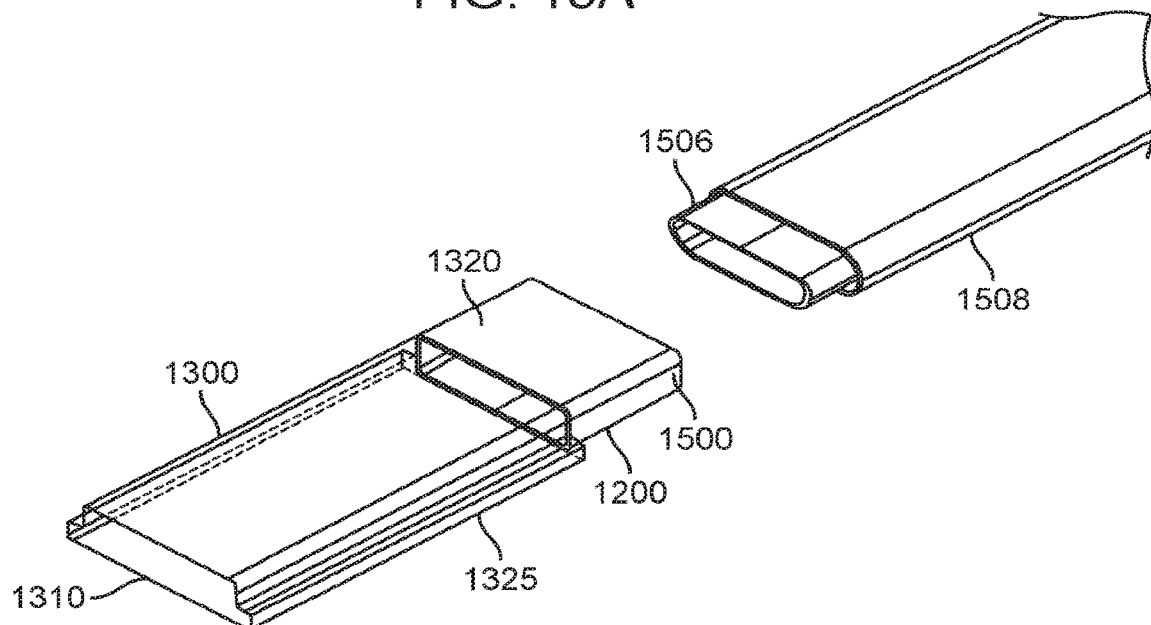
FIG. 15B shows the embodiment of FIG. 15A with the collar disposed over the illumination element.

FIG. 15B shows the embodiment of FIG. 15A and further shows how the collar 1500 may be disposed over at least a portion of the waveguide 1300 and the coupling bracket 1200. The collar may comprise a rectangular, square or other geometrically shaped tube. The tube may define a central channel sized to receive, protect, support, or secure the coupling interface between any of the illumination element 300, the coupling bracket 1200, and the fiber optic input 1506. The collar may also provide strain relief for the various components of the apparatus or device.

Figure 16A:
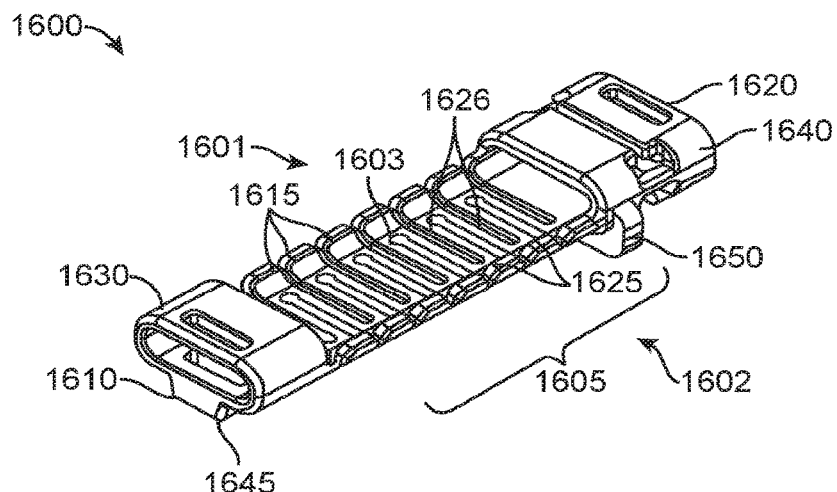
FIGS. 16A-16D show a perspective view, an end view, a top view, and a side view respectively of an embodiment of an articulated track attachment.

FIG. 16A shows a perspective view of an embodiment of an articulated track attachment for attaching a fiber optic input to a surgical instrument. The articulated track attachment 1600 may comprise a proximal end 1620, a distal end 1610, and two sides 1601 and 1602. The articulated track attachment may further comprise a plurality of rails 1626 separated by alternating slots 1625 and aligned to form a flexible track 1605 that extends between the proximal end 1620 and distal end 1610. The proximal end 1620 may comprise a coupling element 1640. The distal end 1610 may comprise a coupling element 1630. The coupling elements 1640 and 1630 may be configured to receive the fiber optic input (not shown) and to attach to the surgical instrument (not shown). The surgical instrument may comprise one or more receptacles (not shown) and the coupling elements may comprise one or more protrusions 1645, 1650, and 1660 for snap-fitting into the receptacles to attach the articulated track attachment 1600 to the surgical instrument. The articulated track attachment 1600 may further comprise a plurality of protrusions 1615 aligned on each of the two sides 1601 and 1602 to form a central channel 1603 and configured to receive the fiber optic input (not shown). The central channel 1603 may be configured to contain and guide the fiber optic input. The articulated track may be configured to conform to angles of between −180 and 180 degrees, wherein an angle of 0 degrees corresponds to an unflexed flat position. By enabling the fiber optic input to substantially conform to the shape of the surgical instrument, the articulated track attachment device may be used to facilitate the coupling and mating of the fiber optic input with the surgical instrument in a low-profile configuration and may also be used to support the fiber optic input and prevent it from kinking. The surgical instrument may comprise a camera, a sensor or a retractor.

Figure 16B:
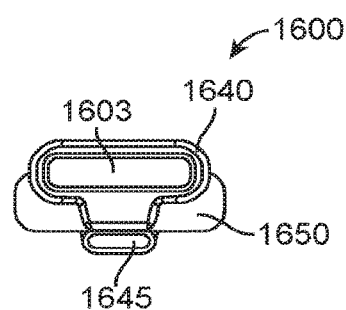
Figure 16C:
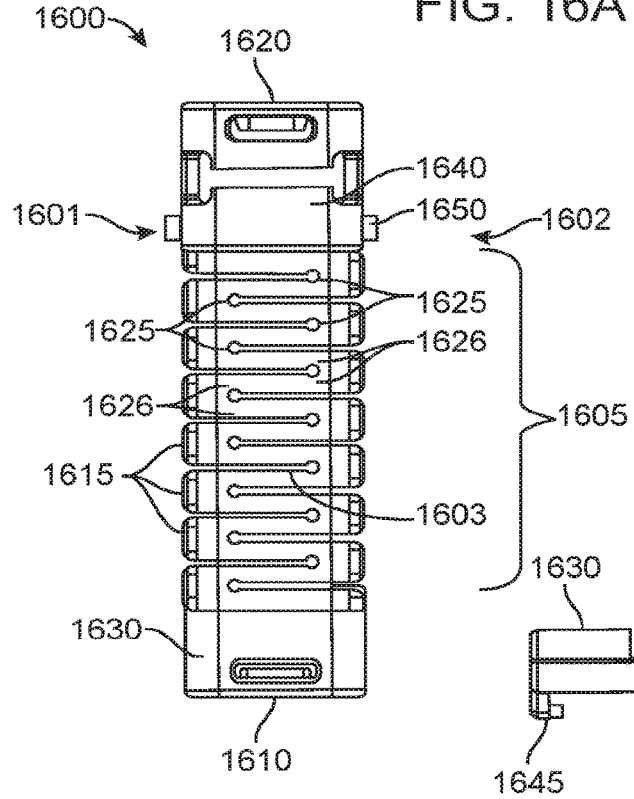
Figure 16D:
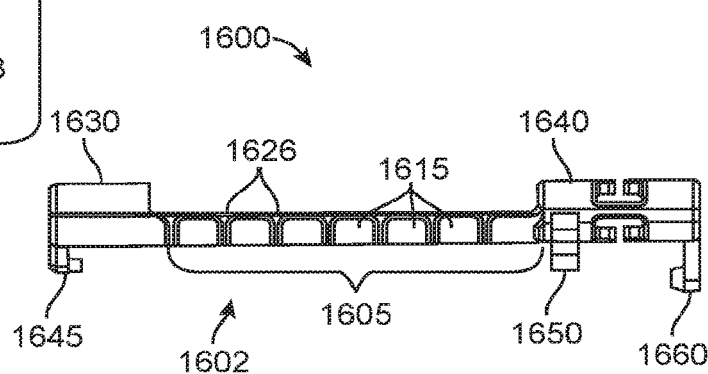

FIGS. 16B-16D show an end view, top view, and side view respectively of the articulated track attachment of FIG. 16A. The articulated track attachment 1600 in FIGS. 16A-16D is shown substantially unflexed at an angle of about 0 degrees.

Figure 17A:
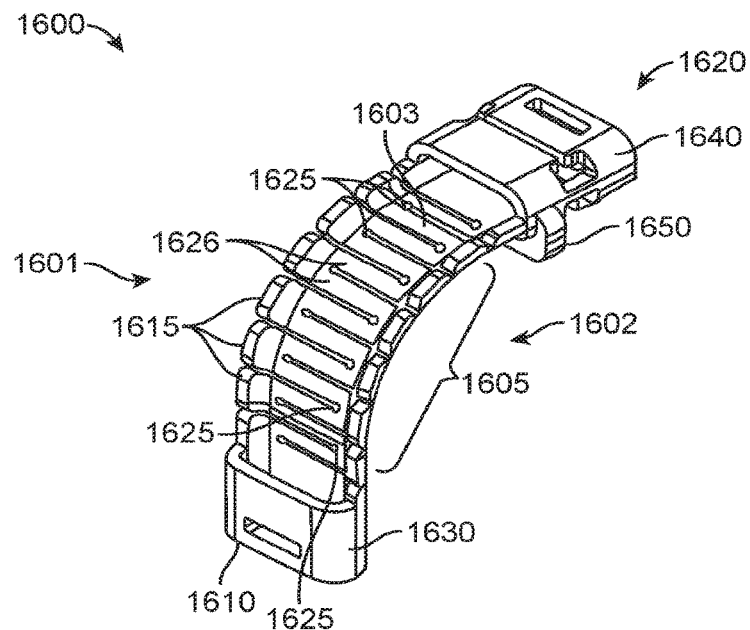
FIGS. 17A-17C show a perspective view, an end view, and a side view respectively of an embodiment of an articulated track attachment flexed.
Figure 17B:
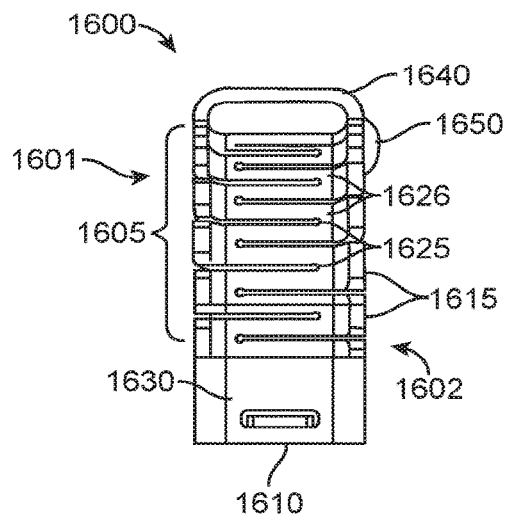
Figure 17C:
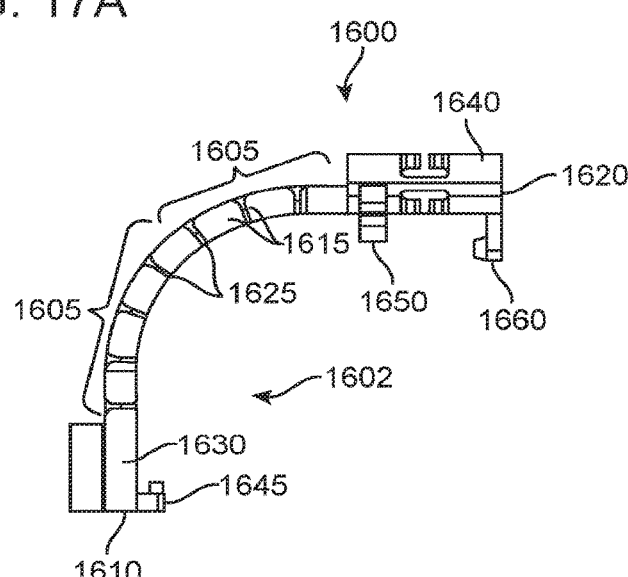

FIGS. 17A-17C show a perspective view, an end view, and a side view respectively of an embodiment of an articulated track attachment shown flexed to conform to an angle of about 90 degrees.

Figure 18A:
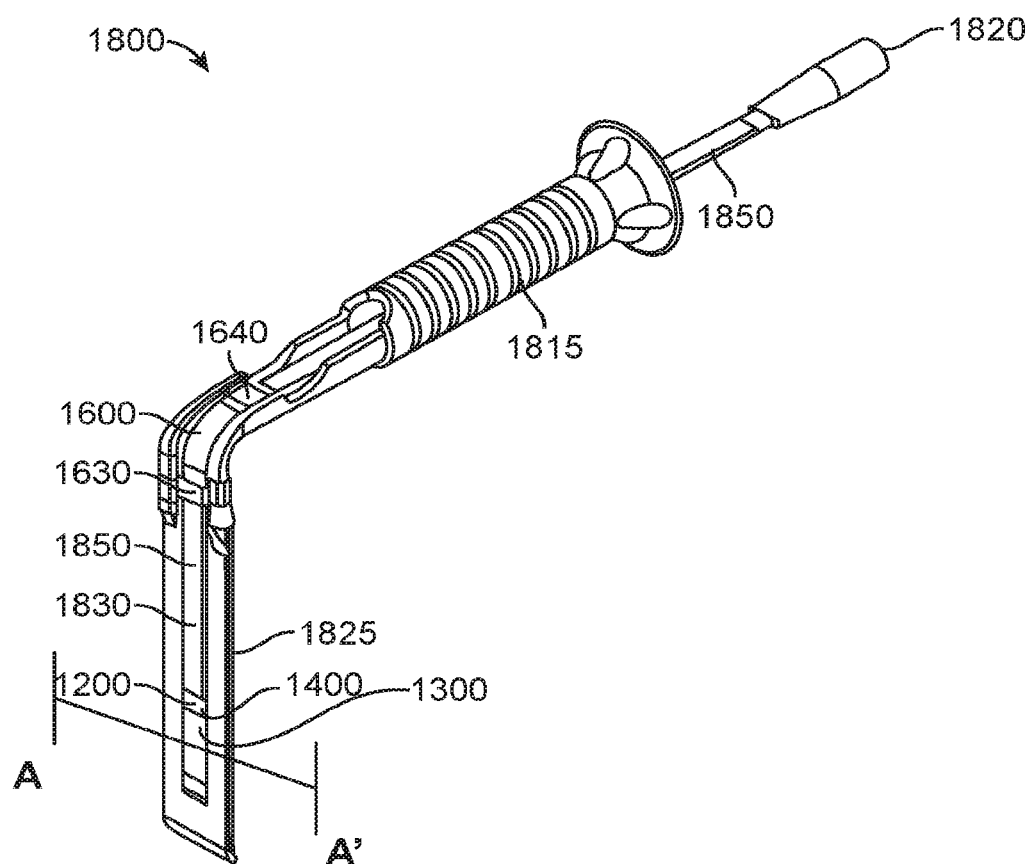
FIG. 18A shows a perspective view of an embodiment of an illuminated surgical apparatus comprising a surgical retractor coupled to an optical waveguide, a fiber optic input, a coupling bracket, a collar, and an articulated track attachment device.

FIG. 18A shows a perspective view of an embodiment of an illuminated surgical apparatus comprising a surgical retractor 1800 coupled to an optical waveguide 1300, a fiber optic input 1850, a coupling bracket (not visible), a collar 1700, and an articulated track attachment device 1600. The surgical retractor may comprise a blade 1825 on its distal end 1810 and a handle 1815 on its proximal end 1820. The surgical retractor blade 1825 may comprise a central channel 1830 for containing the fiber optic input 1850, which may be coupled to the optical waveguide 1300 by the coupling bracket 1200. The coupling bracket may be protected by the collar 1700, which may be disposed over at least a portion of the waveguide 1300, the coupling bracket 1200, and the fiber optic input 1850. The articulated track attachment device 1600 may be flexed to conform to about a 90 degree angle for supporting the fiber optic input 1850, prevent it from kinking, and to conform to the shape of the surgical retractor 1800. The articulated track attachment device thus facilitates coupling and mating of the fiber optic input 1850 with the surgical retractor 1800 in a low-profile configuration.

Figure 18B:
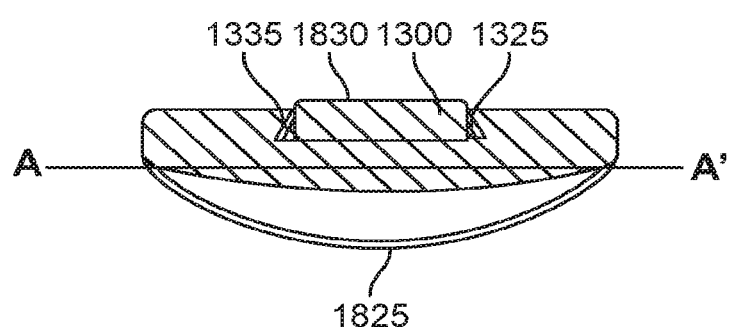
FIG. 18B shows a cross-sectional view of the surgical retractor blade of FIG. 18A taken where the waveguide is coupled to the blade.

FIG. 18B shows a cross-sectional view of the surgical retractor blade of FIG. 18A taken along line A-A' in FIG. 18A where the waveguide 1300 is coupled to the blade 1825. The waveguide 1300 may comprise a protrusion 1325 configured to slide into a receptacle 1335 in the central channel 1830 of the blade.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical illumination apparatus for illuminating a surgical field in a patient, comprising:
   a fiber optic input comprising one or more optical fibers;
   a surgical device comprising:
      a handle having a center channel that extends through the handle, wherein the fiber optic input extends through the center channel, and
      a retractor blade extending from the handle, wherein the retractor blade comprises an elongated receptacle, and
   an optical waveguide coupled to the elongate receptacle of the retractor blade, wherein a proximal end of the optical waveguide is coupled with the fiber optic input and a distal end of the optical waveguide is configured to emit light from the optical waveguide; and
   an optical coupling bracket for coupling the fiber optic input to the optical waveguide, wherein the optical coupling bracket comprises an elongate frame having a proximal end, a distal end, and a central channel extending between the proximal end and the distal end of the elongate frame,
   wherein the central channel of the optical coupling bracket is sized to receive and support the one or more optical fibers,
   wherein the distal end of the optical coupling bracket is coupled to the optical waveguide,
   wherein the optical waveguide comprises a first surface that faces toward the retractor blade and a second surface that faces away from the retractor blade when the optical waveguide is coupled to the elongate receptacle of the retractor blade, and
   wherein the optical waveguide further comprises a first side wall extending between the first surface and the second surface, and a second side wall extending between the first surface and the second surface, wherein the first side wall and the second side wall are opposing sides of the optical waveguide, and
   wherein the first side wall and the second side wall comprise respective protrusions that taper outwardly along a direction from the second surface towards the first surface.

2. The surgical illumination apparatus of claim 1, wherein the optical waveguide is coupled to the elongate receptacle of the retractor blade such that the optical waveguide is slidable relative to the retractor blade.

3. The surgical illumination apparatus of claim 1, further comprising an adhesive disposed in the central channel of the optical coupling bracket and fixedly coupling the one or more optical fibers to the elongate frame of the optical coupling bracket.

4. The surgical illumination apparatus of claim 1, wherein the first surface, the second surface, the first side wall, and the second side wall define a dovetail shape of the optical waveguide.

5. The surgical illumination apparatus of claim 4, wherein the elongate receptacle of the retractor blade defines a groove having a dovetail shape that corresponds to the dovetail shape of the optical waveguide.

6. The surgical illumination apparatus of claim 1, wherein the elongate receptacle of the retractor blade comprises a groove defining an aperture at an outer surface of the retractor blade, and wherein a width of the first surface of the optical waveguide is greater than a width of the aperture such that the elongate receptacle retains the optical waveguide in the groove.

7. The surgical illumination apparatus of claim 6, wherein a width of the second surface of the optical waveguide is less than the width of the aperture, and a height of the optical waveguide is greater than a height of the groove such that the second surface of the optical waveguide is outside of the groove when the optical waveguide is coupled to the elongate receptacle of the retractor blade.

8. The surgical illumination apparatus of claim 1, wherein the one or more optical fibers comprises a plurality of optical fibers that arranged in a plurality of linear arrays stacked atop one another.

9. A surgical illumination apparatus for illuminating a surgical field in a patient, comprising:
 a fiber optic input comprising one or more optical fibers;
 a surgical device comprising:
  a handle having a center channel that extends through the handle, wherein the fiber optic input extends through the center channel, and
  a retractor blade extending from the handle, wherein the retractor blade comprises an elongated receptacle, and
 an optical waveguide coupled to the elongate receptacle of the retractor blade, wherein a proximal end of the optical waveguide is coupled with the fiber optic input and a distal end of the optical waveguide is configured to emit light from the optical waveguide; and
 an optical coupling bracket for coupling the fiber optic input to the optical waveguide, wherein the optical coupling bracket comprises an elongate frame having a proximal end, a distal end, and a central channel extending between the proximal end and the distal end of the elongate frame,
 wherein the central channel of the optical coupling bracket is sized to receive and support the one or more optical fibers,
 wherein the distal end of the optical coupling bracket is coupled to the optical waveguide,
 wherein optical coupling bracket comprises a plurality of protruding members on the proximal end of elongate frame, and
 wherein the plurality of protruding members extend proximally from the central channel of the optical coupling bracket with the one or more optical fibers between the plurality of protruding members.

10. The surgical illumination apparatus of claim 9, wherein the plurality of protruding members extend proximally in a direction that is perpendicular to a longitudinal axis of the optical coupling bracket.

11. The surgical illumination apparatus of claim 9, further comprising an adhesive disposed in the central channel of the optical coupling bracket and fixedly coupling the one or more optical fibers to the elongate frame of the optical coupling bracket.

12. A method for coupling a fiber optic input to an illuminated surgical instrument, said method comprising:
 providing a surgical device comprising: (i) a handle having a center channel that extends through the handle, and (ii) a retractor blade extending from the handle, wherein the retractor blade comprises an elongated receptacle;
 coupling a fiber optic input to the handle by inserting the fiber optic input through the center channel in the handle, wherein the fiber optic input comprises one or more optical fibers;
 coupling an optical waveguide to the retractor blade of the surgical device by inserting the optical waveguide in the elongated receptacle of the retractor blade,
 wherein an optical coupling bracket couples the fiber optic input to the optical waveguide,
 wherein the optical coupling bracket comprises an elongate frame having a proximal end, a distal end, and a central channel extending between the proximal end and the distal end of the elongate frame,
 wherein optical coupling bracket comprises a plurality of protruding members on the proximal end of elongate frame, and
 wherein the plurality of protruding members extend proximally from the central channel of the optical coupling bracket with the one or more optical fibers between the plurality of protruding members.

13. The method of claim 12, further comprising coupling the optical coupling bracket to the optical waveguide and coupling the optical coupling bracket to the fiber optic input.

14. The method of claim 13, wherein coupling the optical coupling bracket to the optical waveguide comprises adhesively bonding a distal end of the elongate frame of the optical coupling bracket to the optical waveguide.

15. The method of claim 13, further comprising at least one of trimming the one or more optical fibers while the one or more optical fibers are in the central channel of the optical coupling bracket.

16. The method of claim 13, wherein coupling the optical coupling bracket to the fiber optic input comprises disposing the fiber optic input in the central channel of the optical coupling bracket and arranging the one or more optical fibers of the fiber optic input in a plurality of linear arrays that are vertically stacked atop one another.

17. The method of claim 16, wherein disposing the fiber optic input in the central channel further comprises adhesively bonding the one or more optical fibers of the fiber optic input with the elongate frame of the optical coupling bracket.

18. The method of claim 12, further comprising sliding the optical waveguide in the elongate receptacle of the retractor blade.

19. The method of claim 12, wherein the optical waveguide comprises a first surface that faces toward from the retractor blade and a second surface that faces away the retractor blade when the optical waveguide is coupled to the elongate receptacle of the retractor blade, and
 wherein the optical waveguide further comprises a first side wall extending between the first surface and the second surface, and a second side wall extending between the first surface and the second surface, wherein the first side wall and the second side wall are opposing sides of the optical waveguide, and
 wherein the first side wall and the second side wall comprise respective protrusions that taper outwardly along a direction from the second surface towards the first surface.

20. The method of claim 19, wherein the elongate receptacle of the retractor blade comprises a groove defining an aperture at an outer surface of the retractor blade, and
 wherein a width of the first surface of the optical waveguide is greater than a width of the aperture such that the elongate receptacle retains the optical waveguide in the groove.

* * * * *